(12) United States Patent
Lahiri et al.

(10) Patent No.: US 8,901,322 B2
(45) Date of Patent: Dec. 2, 2014

(54) CRYSTALLINE FORMS OF CABAZITAXEL AND PROCESS FOR PREPARATION THEREOF

(71) Applicant: Fresenius Kabi Oncology Limited, New Delhi (IN)

(72) Inventors: Saswata Lahiri, Gurgaon (IN); Rajesh Srivastava, Gurgaon (IN); Bhuwan Bhaskar Mishra, Gurgaon (IN); Shatrughan Sharma, Gurgaon (IN); Vijay Ojha, Gurgaon (IN); Nilendu Panda, Gurgaon (IN); Sandeep Kumar, Gurgaon (IN); Sonu Prasad, Gurgaon (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 0 days.

(21) Appl. No.: 13/683,062

(22) Filed: Nov. 21, 2012

(65) Prior Publication Data

US 2013/0211109 A1     Aug. 15, 2013

(30) Foreign Application Priority Data

Nov. 28, 2011 (IN) ............................ 3405/DEL/2011

(51) Int. Cl.
    *C07D 321/00*      (2006.01)
    *C07D 305/14*      (2006.01)

(52) U.S. Cl.
    CPC ................................... *C07D 305/14* (2013.01)
    USPC ........................................................ 549/351

(58) Field of Classification Search
    USPC ........................................................ 549/351
    See application file for complete search history.

(56) References Cited

U.S. PATENT DOCUMENTS 5,670,673 A * 9/1997 Rao .............................. 549/510
7,241,907 B2    7/2007 Didier et al.

FOREIGN PATENT DOCUMENTS

WO      2009/115655      9/2009

OTHER PUBLICATIONS

Caira, "Crystalline Polymorphism of Organic Compounds," Topics in Chemistry, vol. 198, pp. 163-208 (1998).

* cited by examiner

*Primary Examiner* — Andrew D Kosar
*Assistant Examiner* — Raymond Covington
(74) *Attorney, Agent, or Firm* — Occhiuti & Rohlicek LLP

(57) ABSTRACT

The present invention provides Crystalline Forms of 4-acetoxy-2α-benzoyloxy-5β-20-epoxy-1-hydroxy-7β,10β-dimethoxy-9-oxotax-11-en-13α-yl(2R,3S)-3-tert-butoxy-carbonylamino-2-hydroxy-3-phenylpropionate, i.e Cabazitaxel. The present invention also discloses methods for the preparation of Crystalline Forms of Cabazitaxel and pharmaceutical compositions thereof.

30 Claims, 26 Drawing Sheets

CRYSTALLINE FORMS OF CABAZITAXEL AND PROCESS FOR PREPARATION THEREOF

FIELD OF THE INVENTION

Figure 1:
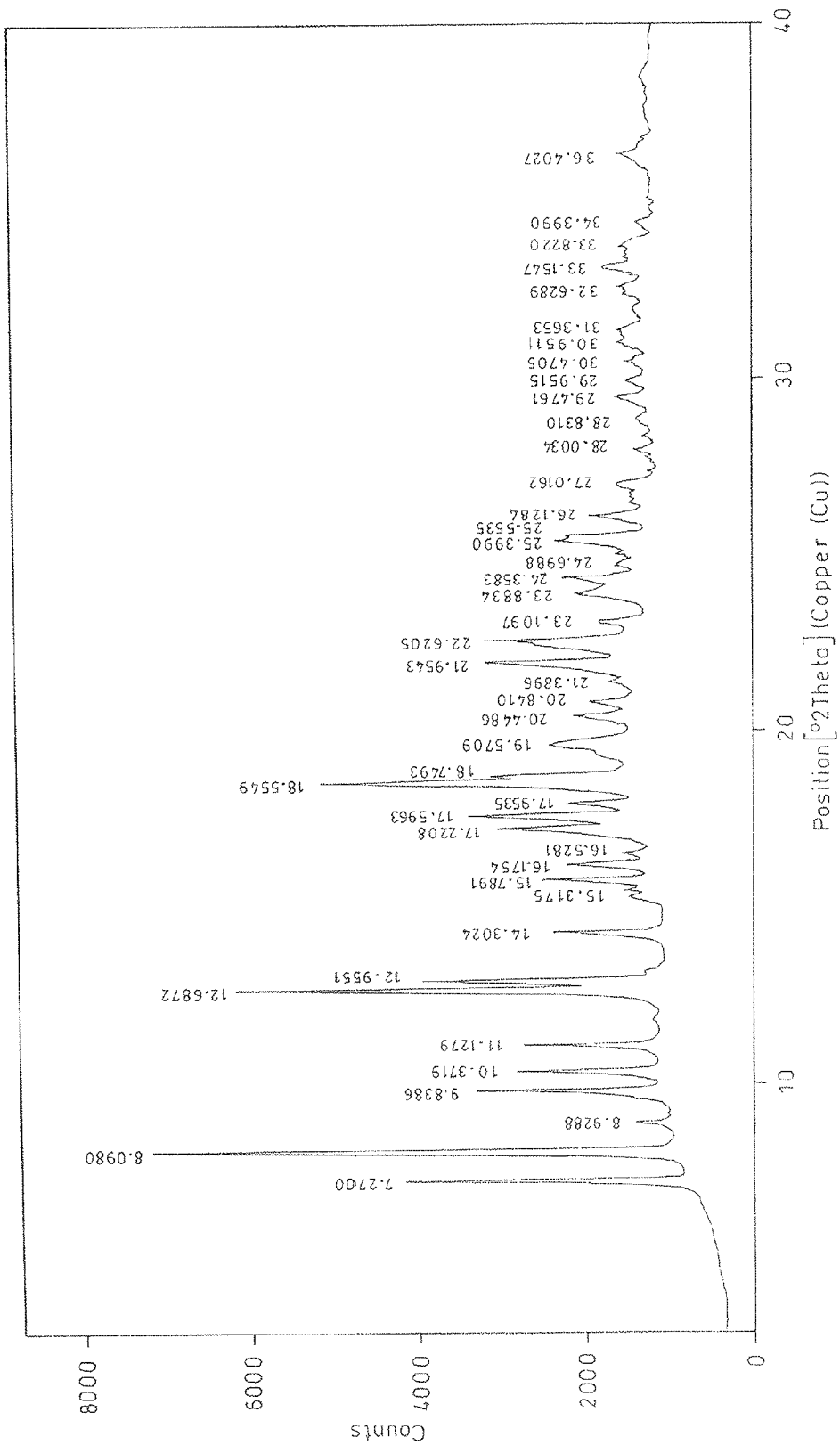

The present invention relates to the Crystalline Forms of 4-acetoxy-2α-benzoyloxy-5β-20-epoxy-1-hydroxy-7β,10β-dimethoxy-9-oxotax-11-en-13α-yl(2R,3S)-3-tert-butoxycarbonylamino-2-hydroxy-3-phenylpropionate, i.e Cabazitaxel, methods for its preparation and pharmaceutical compositions thereof.

BACK GROUND OF THE INVENTION

Cabazitaxel, chemically known as 4-acetoxy-2α-benzoyloxy-5β,20-epoxy-1-hydroxy-7β,10β-dimethoxy-9-oxotax-11-en-13α-yl(2R,3S)-3-tert-butoxycarbonylamino-2-hydroxy-3-phenylpropionate, is represented by Formula (I).

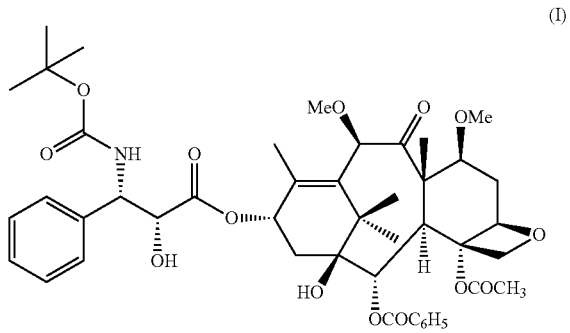

(I)

It is a microtubule inhibitor, indicated in combination with prednisone for treatment of patients with hormone-refractory metastatic prostate cancer previously treated with a docetaxel-containing treatment regimen, under the trade name Jevtana®.

Cabazitaxel is known from U.S. Pat. No. 5,847,170. Process for the preparation of Cabazitaxel is described in U.S. Pat. No. 5,847,170.

The acetone solvate of 4-acetoxy-2α-benzoyloxy-5β-20-epoxy-1-hydroxy-7β,10β-dimethoxy-9-oxotax-11-en-13α-yl-(2R,3S)-3-tert-butoxycarbonylamino-2-hydroxy-3-phenylpropionate (Form A) is formed by crystallization using acetone and is characterized by XRD in U.S. Pat. No. 7,241,907.

US 20110144362 describes anhydrous crystalline Forms B to Form F, ethanolates Form B, D, E and F and mono and dihydrate Forms of Cabazitaxel. All the anhydrous crystalline forms are prepared either by acetone solvate or ethanol solvate. Mono and dihydrate forms are formed at ambient temperature in an atmosphere containing 10 and 60% relative humidity, respectively.

Present invention provides the novel crystalline forms of Cabazitaxel directly from the crude Cabazitaxel.

SUMMARY OF THE INVENTION

The present invention relates to Crystalline Polymorphs of Cabazitaxel and processes for preparing them.

In the first aspect, the present invention relates to Crystalline Cabazitaxel Polymorphs and processes thereof.

These polymorphs are hereinafter referred to as Form-1, Form-2, Form-3, Form-4, Form-5, Form-6, Form-7, Form-8, Form-9, Form-10, Form-11, Form-12, and Form-13.

The crystalline Forms 1 to Form 13 may be characterized using various techniques, which are well known to those of ordinary skill in the art. Examples of characterization methods include, but are not limited to, single crystal X-ray diffraction, powder X-ray diffraction (PXRD), simulated powder X-ray patterns, differential scanning calorimetry (DSC), solid-state 13C-NMR, Raman spectroscopy, infrared spectroscopy, moisture sorption isotherms, thermal gravimetric analysis (TGA), and hot stage techniques.

In general, process for preparing crystalline polymorphic forms of Cabazitaxel may comprise of following steps:
 a) Providing a solution of Cabazitaxel in an organic solvent;
 b) Combining a solution of Cabazitaxel in organic solvent with anti-solvent.
 c) Stirring the solution to get the solid precipitate;
 d) Removing the solvent by filtration to get crystals;
 e) Drying the crystals in vacuum oven at ambient temperature.

Preferred suitable solvents can be alcohols, ketones, ethers, chlorinated hydrocarbons, esters, nitriles, dipolar aprotic solvents, cyclic ethers, and mixtures thereof. In particular the suitable solvents can be methanol, ethanol, isopropanol, dichloromethane, dichloroethane, acetonitrile, tetrahydrofuran, dioxane, diethylether, diisopropylether, methyltertiary butylether, and mixtures thereof.

Present invention provides process for the preparation of crystalline Form-1 of Cabazitaxel, comprising,
 a. dissolving crude Cabazitaxel in chlorinated hydrocarbon.
 a. adding aliphatic hydrocarbon solvent to the solution obtained in step (a); and
 b. isolating Cabazitaxel crystalline Form-1

Present invention provides process for the preparation of crystalline Form-2 of Cabazitaxel, comprising,
 a. dissolving crude Cabazitaxel in dimethyl sulfoxide.
 b. adding water to the solution obtained in step (a); and
 c. isolating Cabazitaxel crystalline Form-2.

Present invention provides process for the preparation of crystalline Form-3 of Cabazitaxel, comprising,
 a. dissolving crude Cabazitaxel in Acetonitrile.
 b. adding water to the solution obtained in step (a); and
 c. isolating Cabazitaxel crystalline Form-3.

Present invention provides process for the preparation of crystalline Form-4 of Cabazitaxel, comprising,
 a. dissolving crude Cabazitaxel in Acetonitrile.
 b. adding the solution obtained in step (a) in to water; and
 c. isolating Cabazitaxel crystalline Form-4.

Present invention provides process for the preparation of crystalline Form-5 of Cabazitaxel, comprising,
 a. dissolving crude Cabazitaxel in Methanol.
 b. adding water to the solution obtained in step (a); and
 b. isolating Cabazitaxel crystalline Form-5.

Present invention provides process for the preparation of crystalline Form-6 of Cabazitaxel, comprising,
 a. dissolving crude Cabazitaxel in Toluene.
 b. cooling the solution obtained in step (a) in refrigerator at 0-5° C.; and
 c. isolating Cabazitaxel crystalline Form-6.

Present invention provides process for the preparation of crystalline Form-7 of Cabazitaxel, comprising,
 a. dissolving crude Cabazitaxel in Tetrahydrofuran.
 b. adding aliphatic hydrocarbon solvent to the solution obtained in step (a); and c. isolating Cabazitaxel crystalline Form-5.

Present invention provides process for the preparation of crystalline Form-8 of Cabazitaxel, comprising,
  a. dissolving crude Cabazitaxel in ethyl acetate.
  b. adding aliphatic hydrocarbon solvent to the solution obtained in step (a); and
  c. isolating Cabazitaxel crystalline Form-8.

Present invention provides process for the preparation of crystalline Form-9 of Cabazitaxel, comprising,
  a. dissolving crude Cabazitaxel in ethyl acetate.
  b. distillation of the solution of step (a) at a suitable temperature; and
  c. isolating Cabazitaxel crystalline Form-9.

Present invention provides process for the preparation of crystalline Form-10 of Cabazitaxel, comprising,
  a. dissolving crude Cabazitaxel in tetrahydrofuran.
  b. adding Methyl tert-butyl ether to the solution obtained in step (a); and
  c. isolating Cabazitaxel crystalline Form-10.

Present invention provides process for the preparation of crystalline Form-11 of Cabazitaxel, comprising,
  a. dissolving crude Cabazitaxel in Dichloromethane.
  b. adding Methyl tert-butyl ether to the solution obtained in step (a); and
  c. isolating Cabazitaxel crystalline Form-11.

Present invention provides process for the preparation of crystalline Form-12 of Cabazitaxel, comprising,
  a. dissolving crude Cabazitaxel in Dichloromethane.
  b. keeping the solution obtained in step (a) at ambient temperature for 2 days; and
  c. isolating Cabazitaxel crystalline Form-12.

Present invention provides process for the preparation of crystalline Form-13 of Cabazitaxel, comprising,
  a. dissolving crude Cabazitaxel in Acetonitrile.
  b. keeping the solution obtained in step (a) at ambient temperature for 2 days; and
  c. isolating Cabazitaxel crystalline Form-13.

In another aspect there is provided a pharmaceutical compositions comprising a therapeutically effective amount of Crystalline Cabazitaxel Form 1 to Form 13 and one or more pharmaceutically acceptable carriers, excipients or diluents.

BRIEF DESCRIPTION OF THE ACCOMPANYING DRAWINGS

Figure 2:
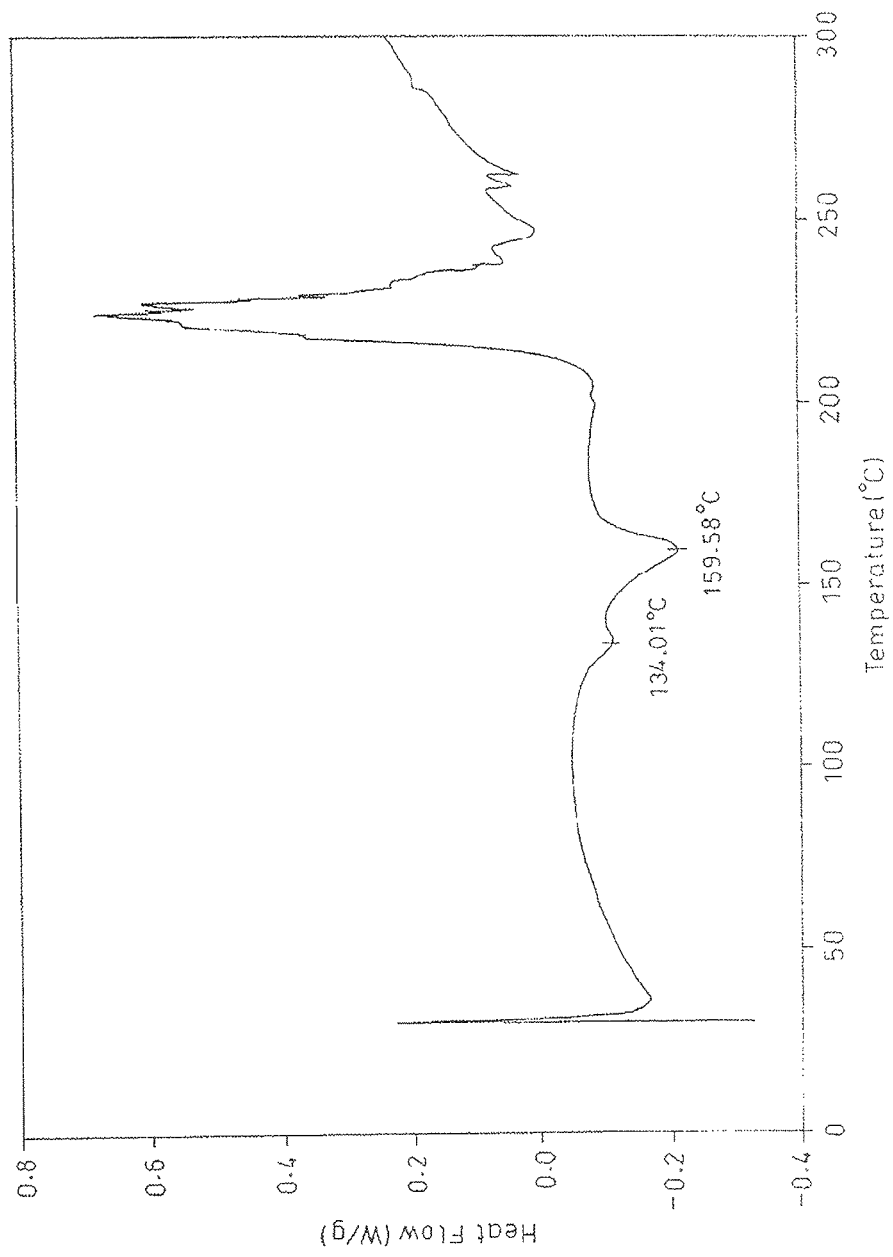
Figure 3:
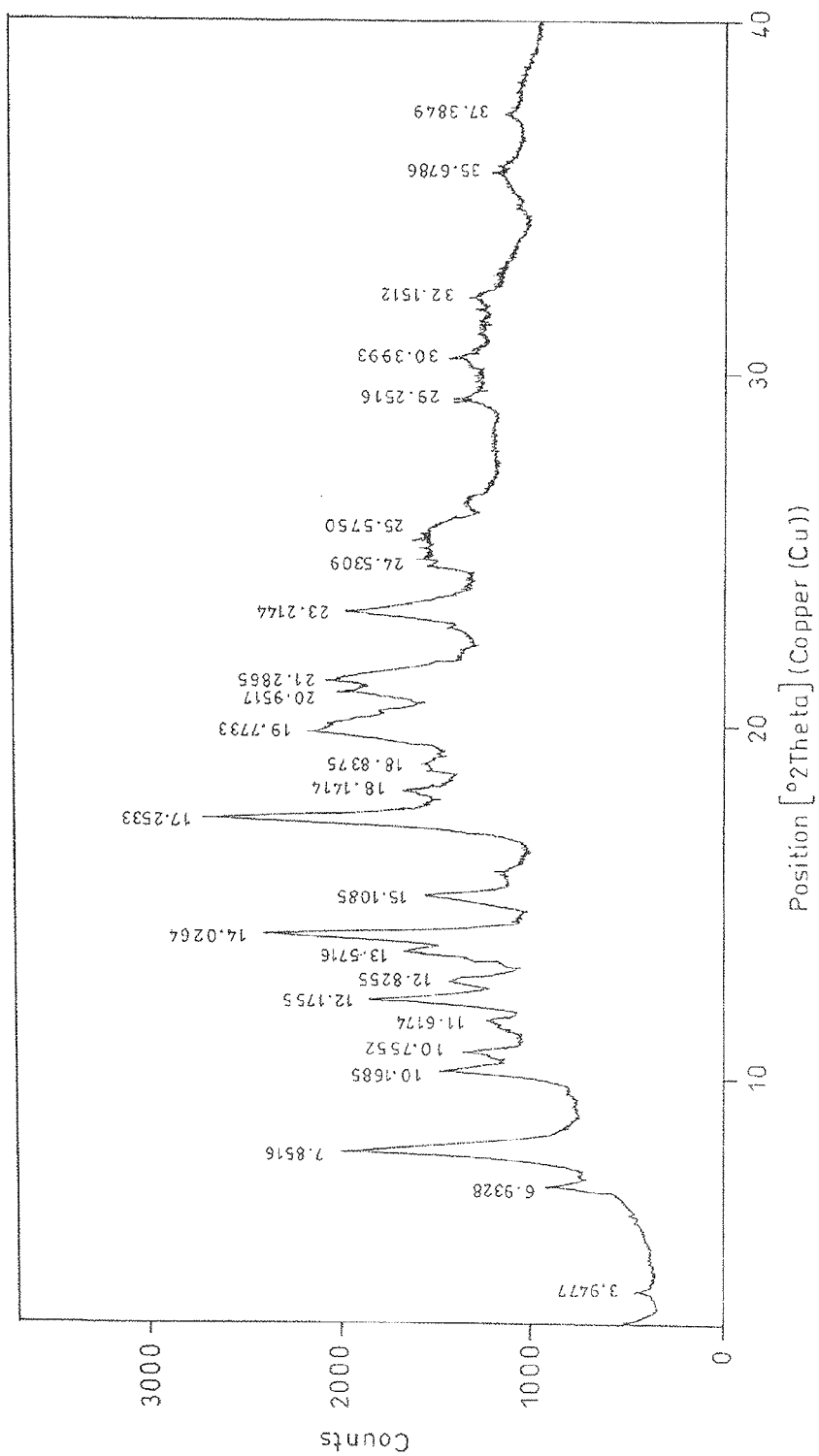
Figure 4:
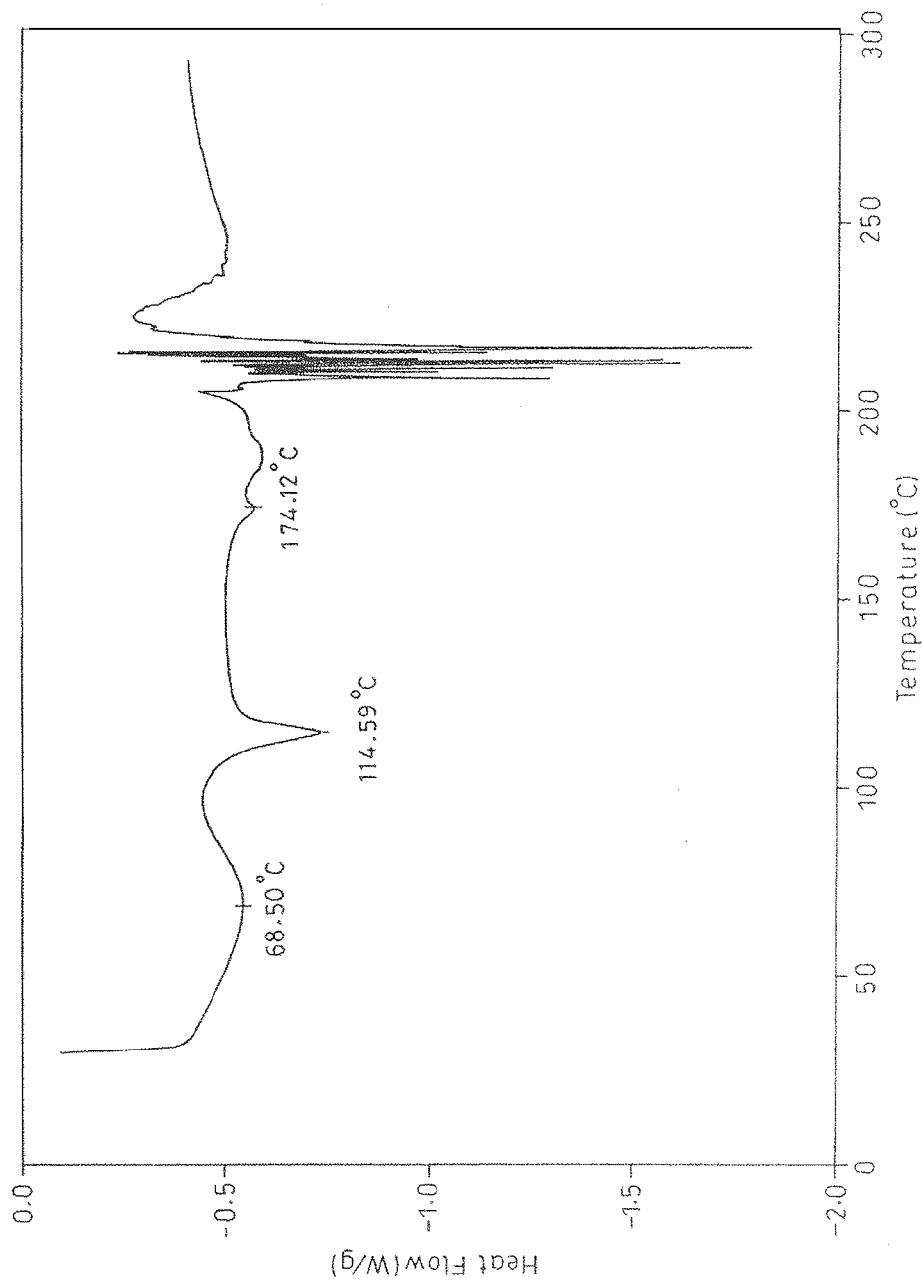
Figure 5:
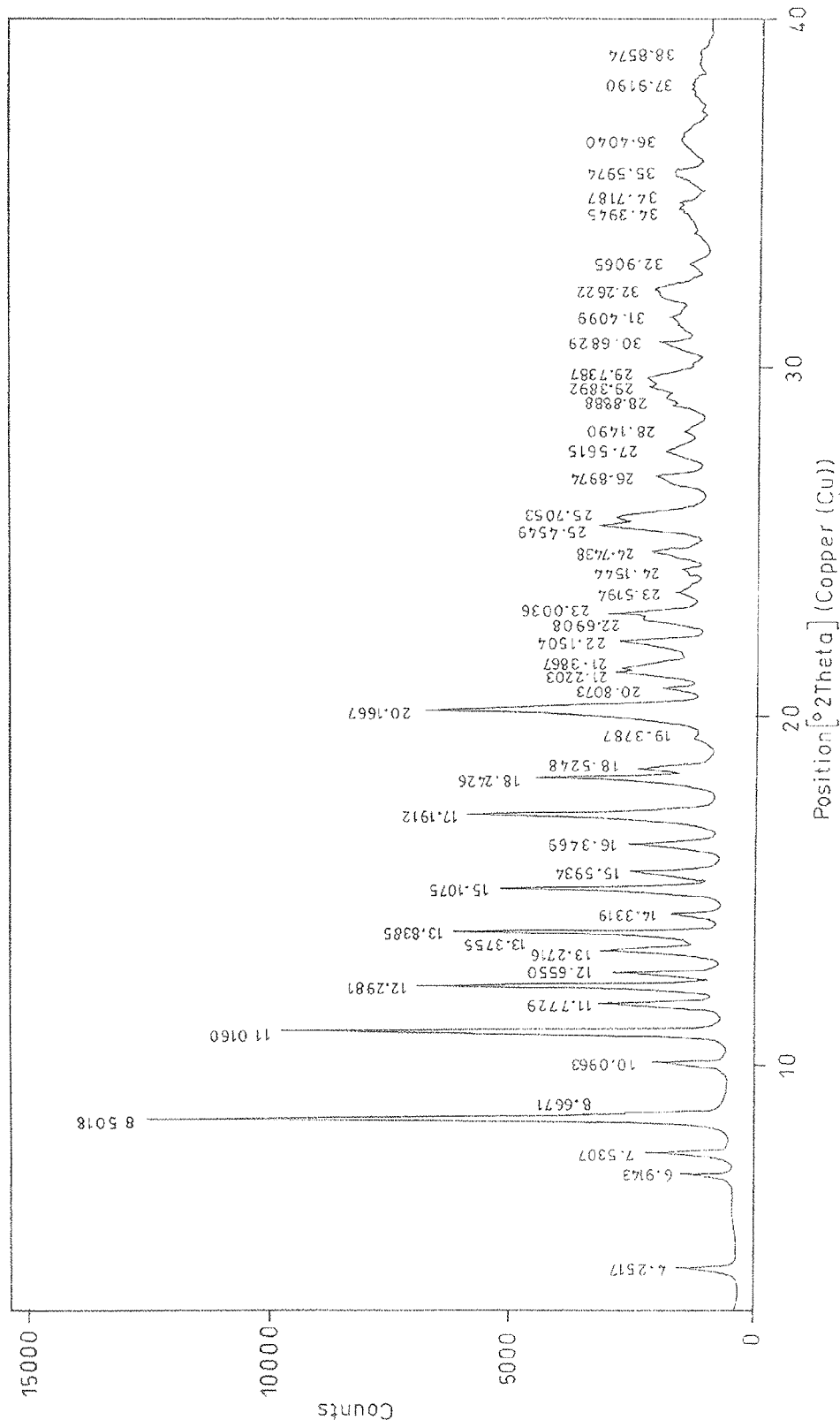
Figure 6:
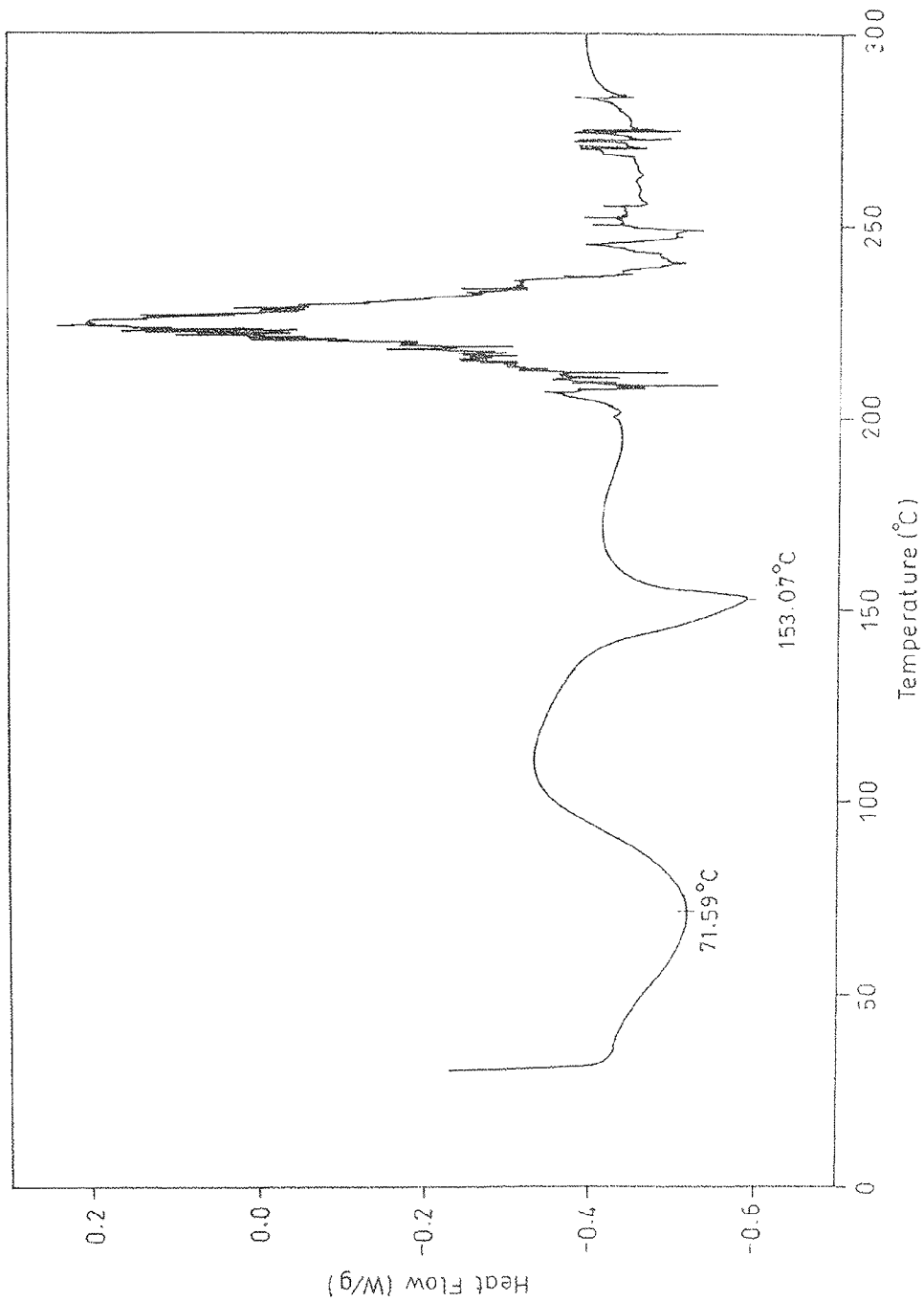
Figure 7:
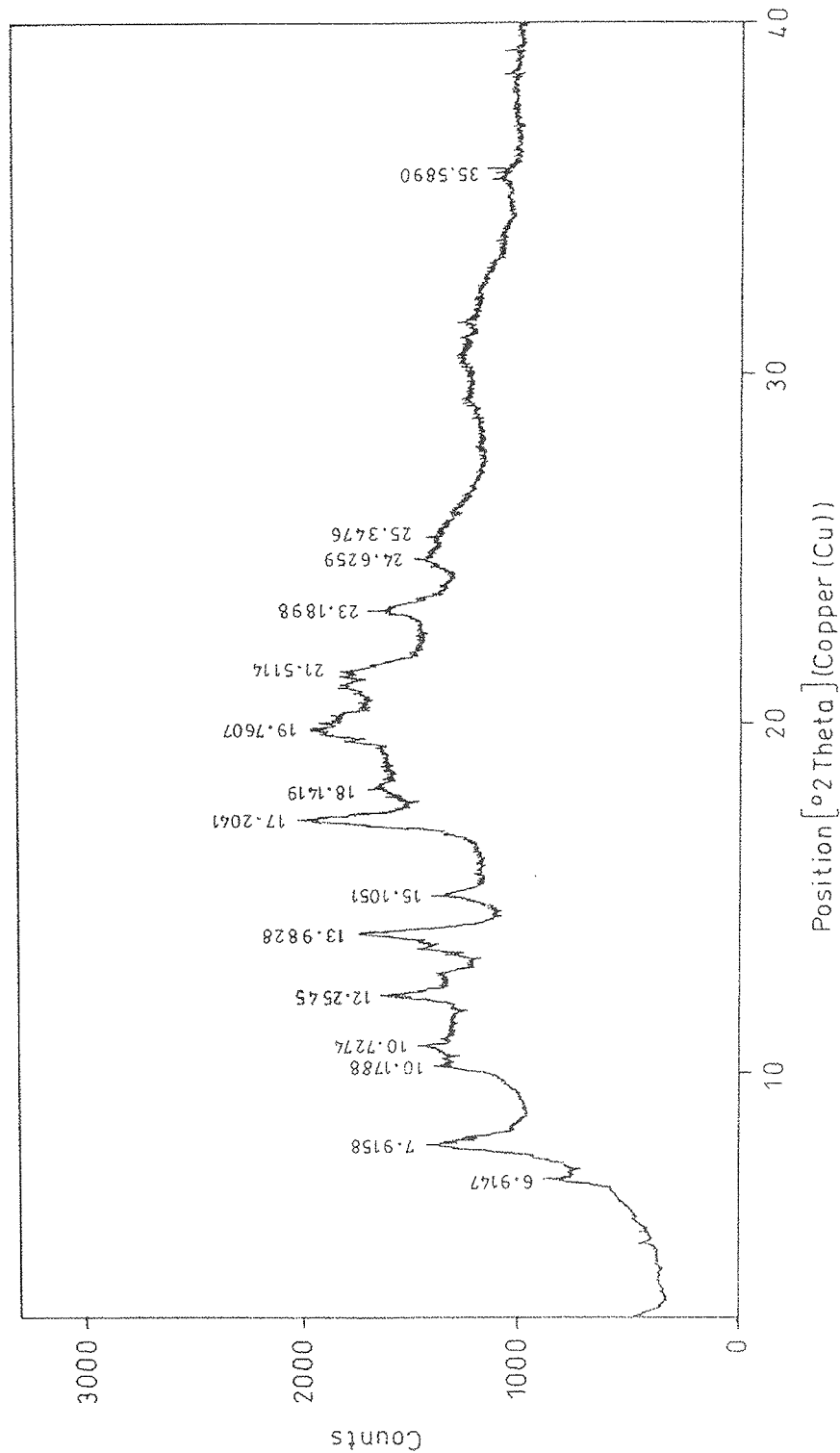
Figure 8:
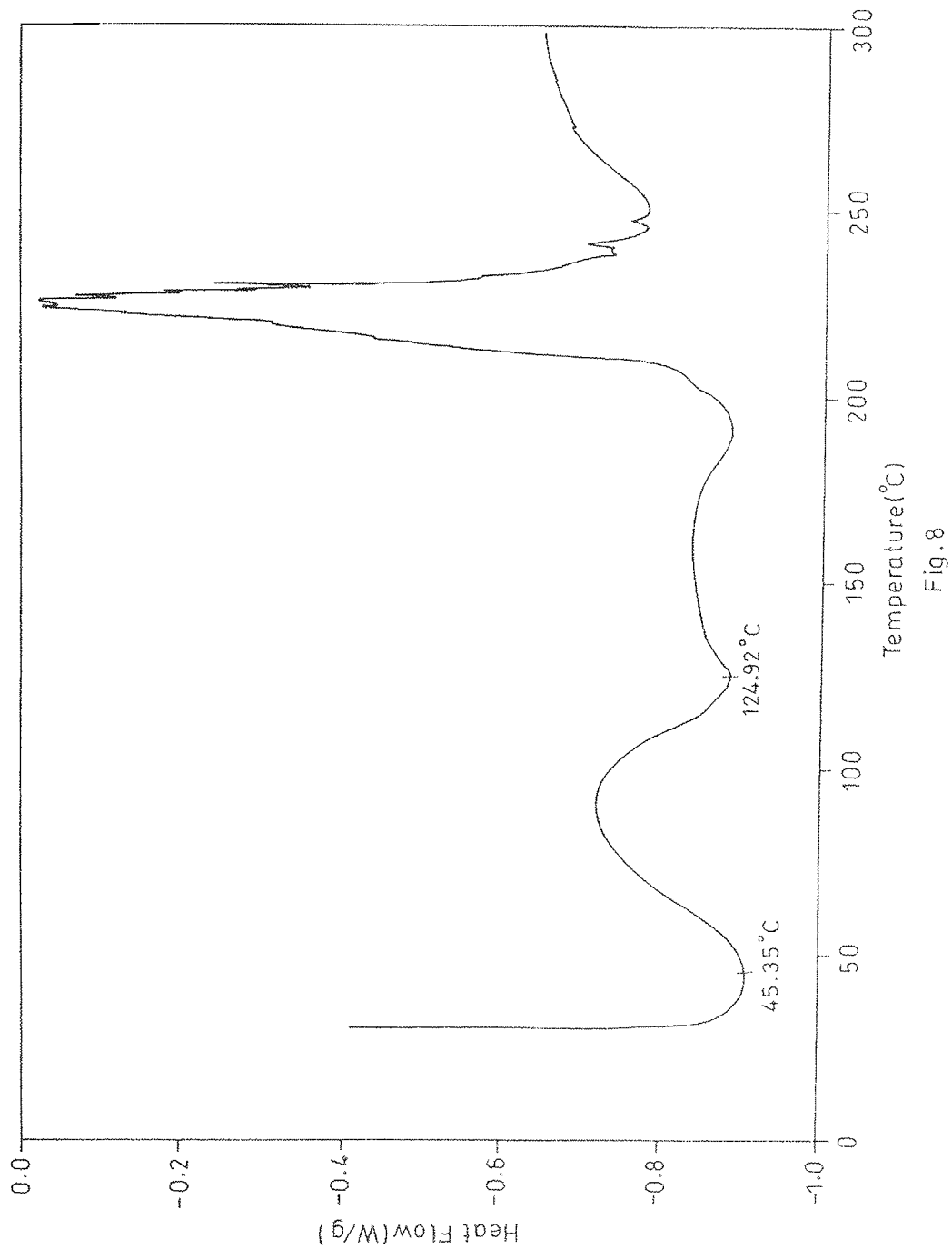
Figure 9:
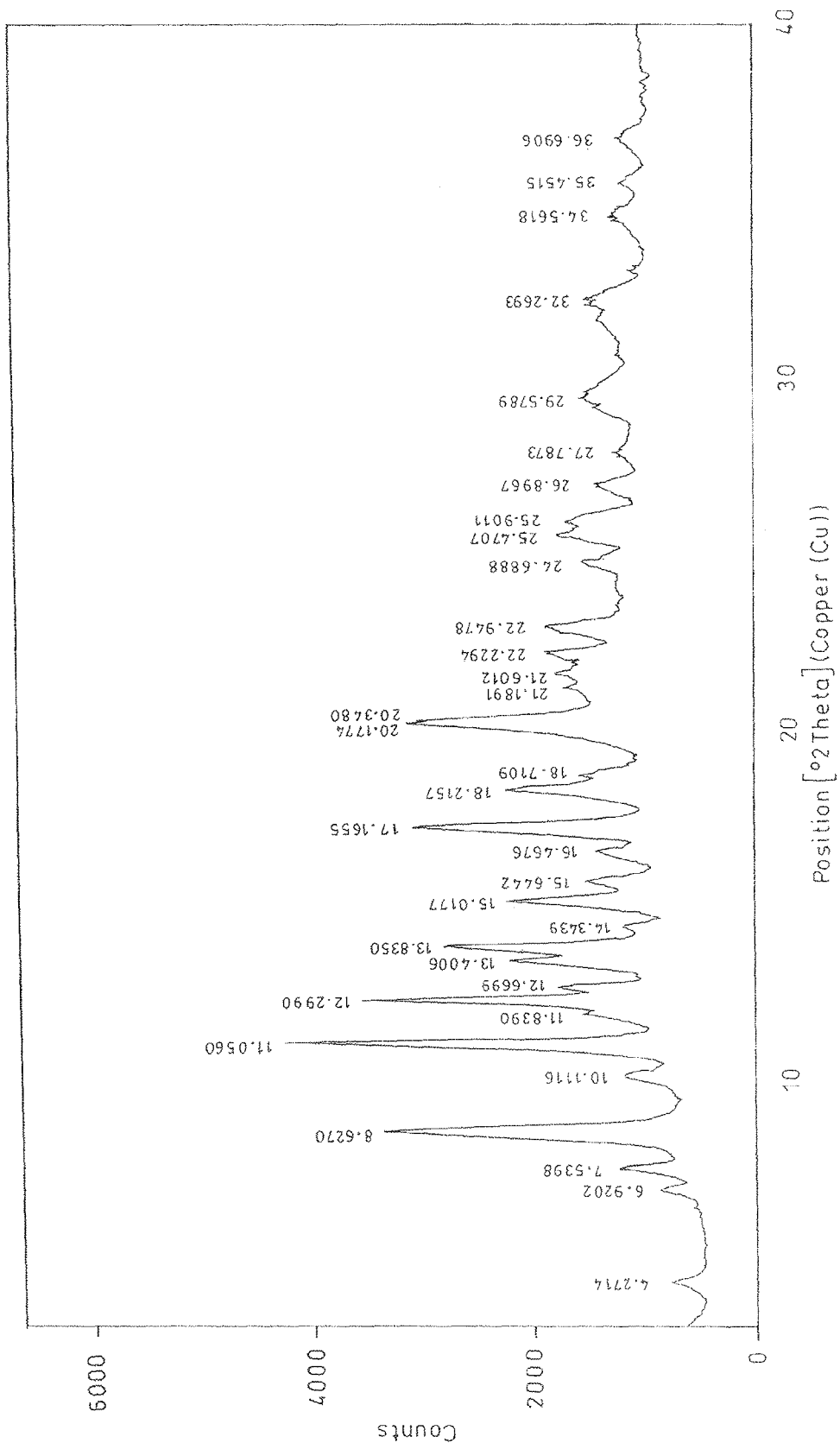
Figure 10:
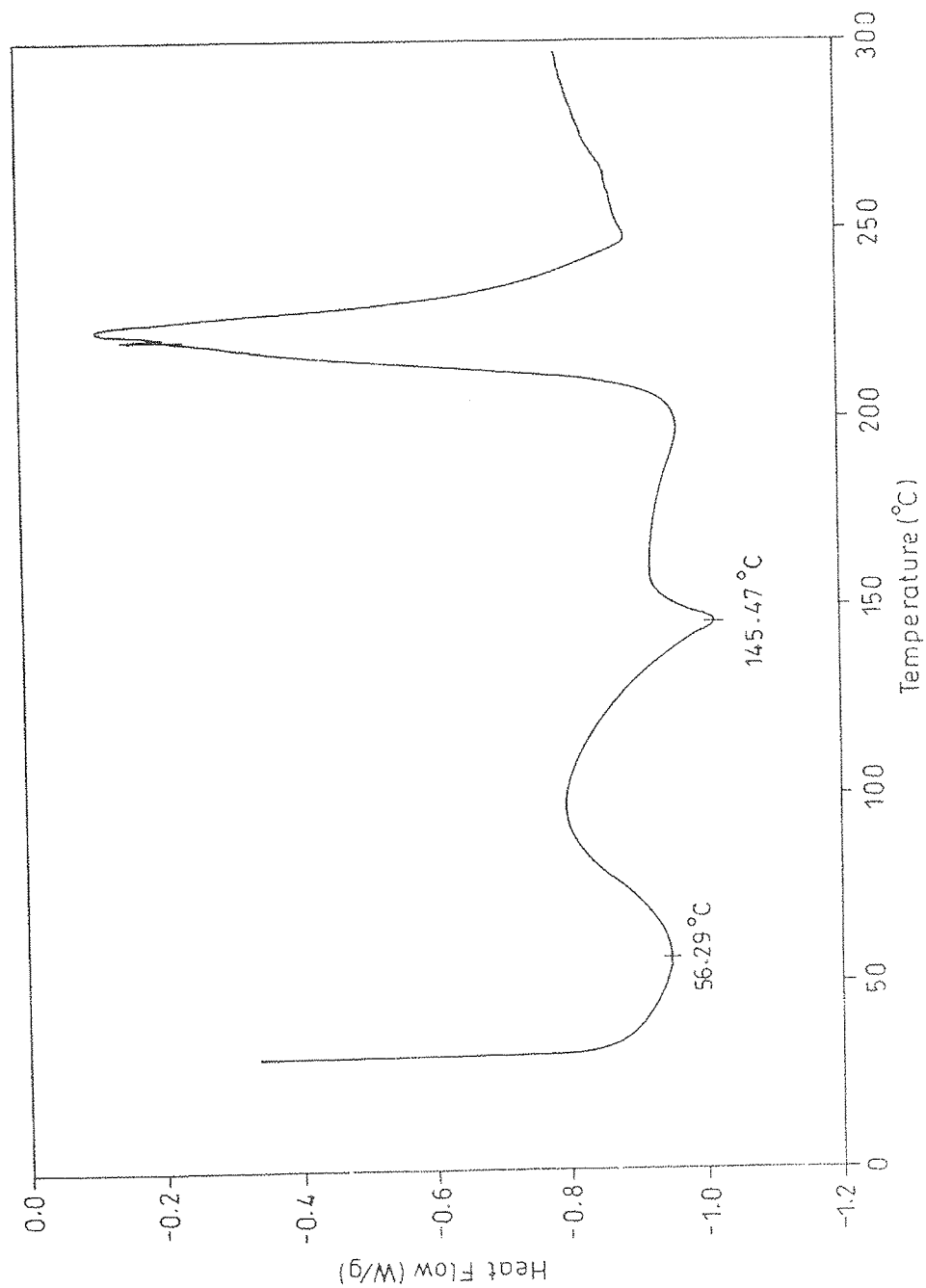
Figure 11:
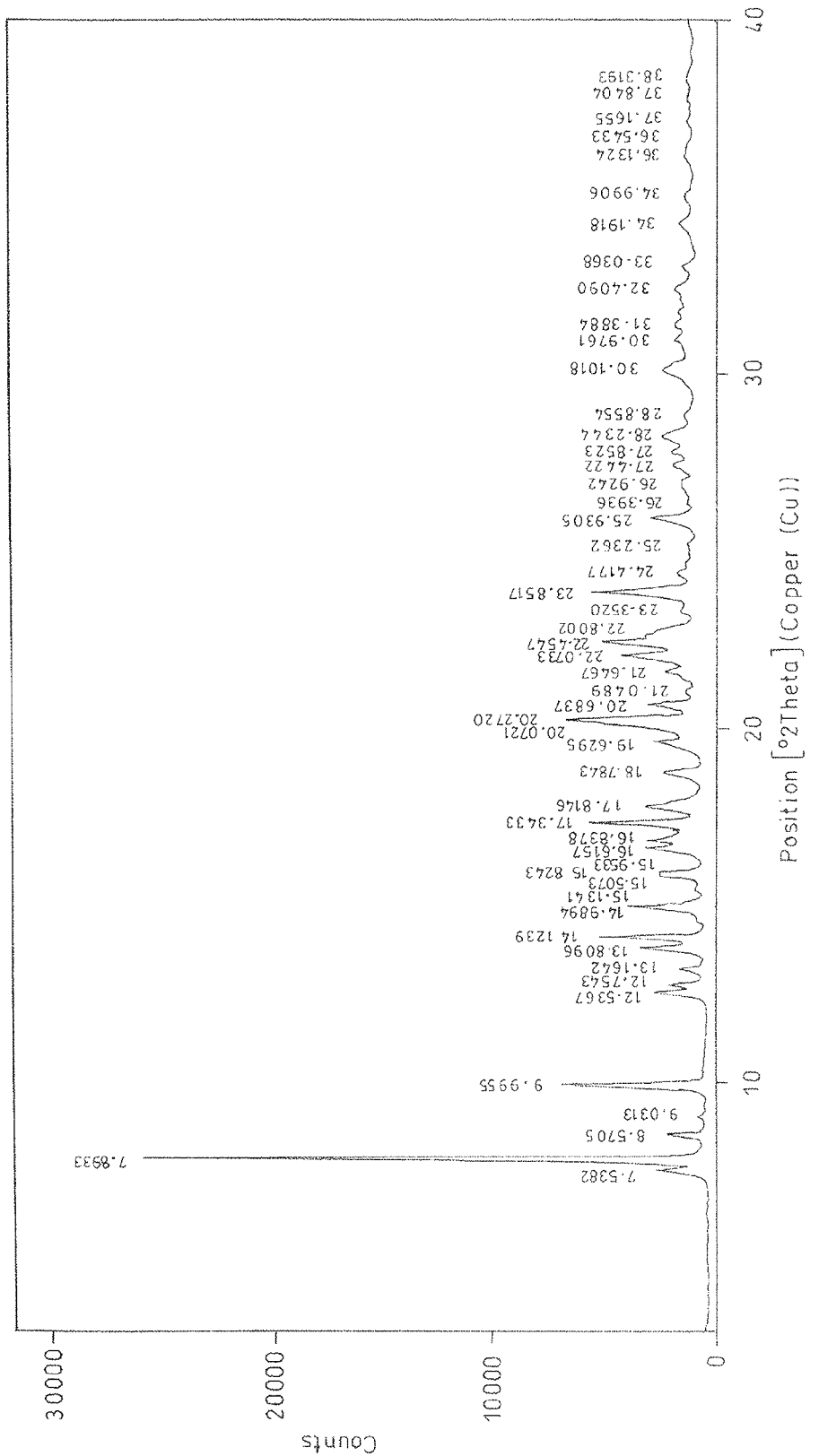
Figure 12:
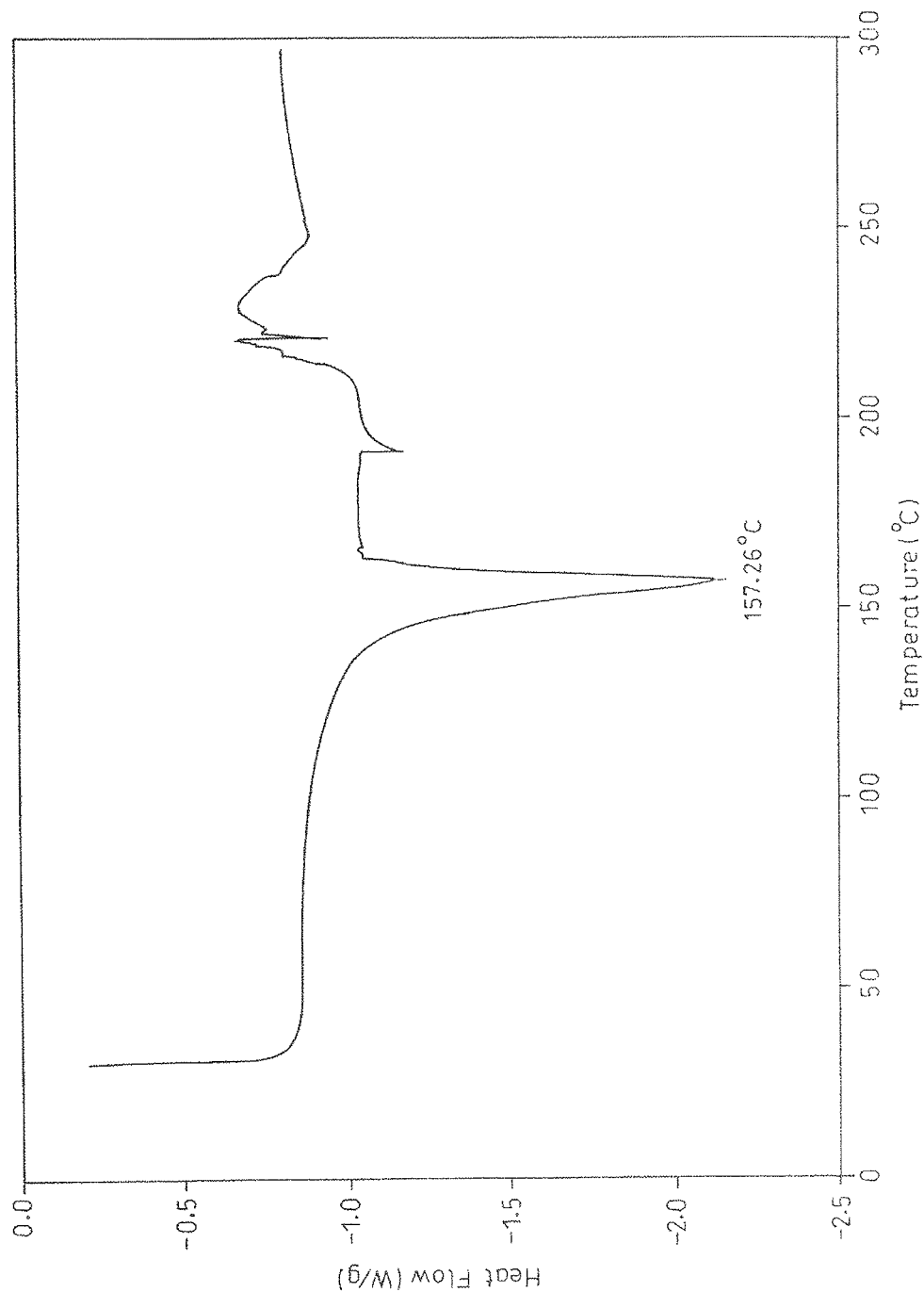
Figure 13:
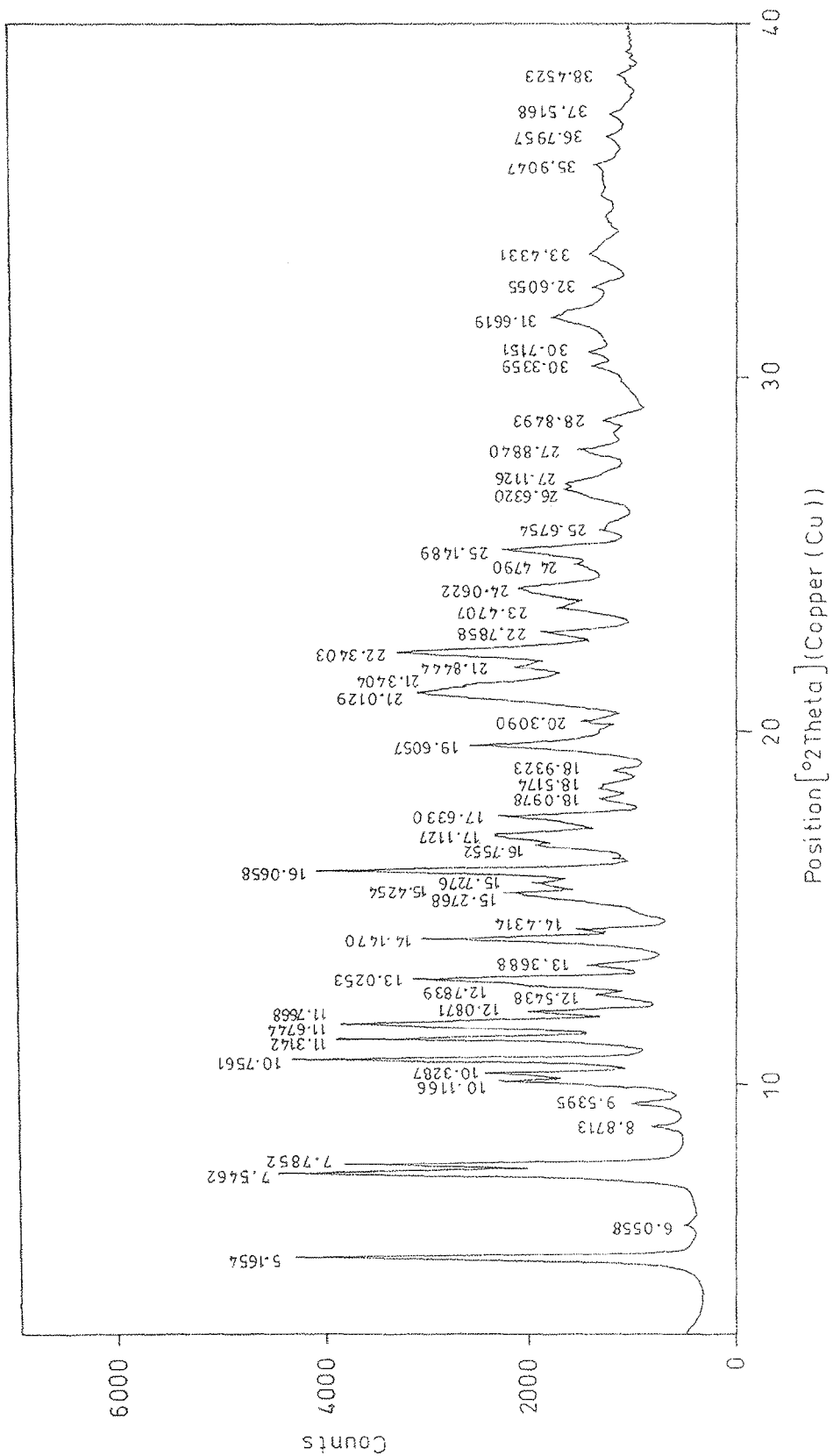
Figure 14:
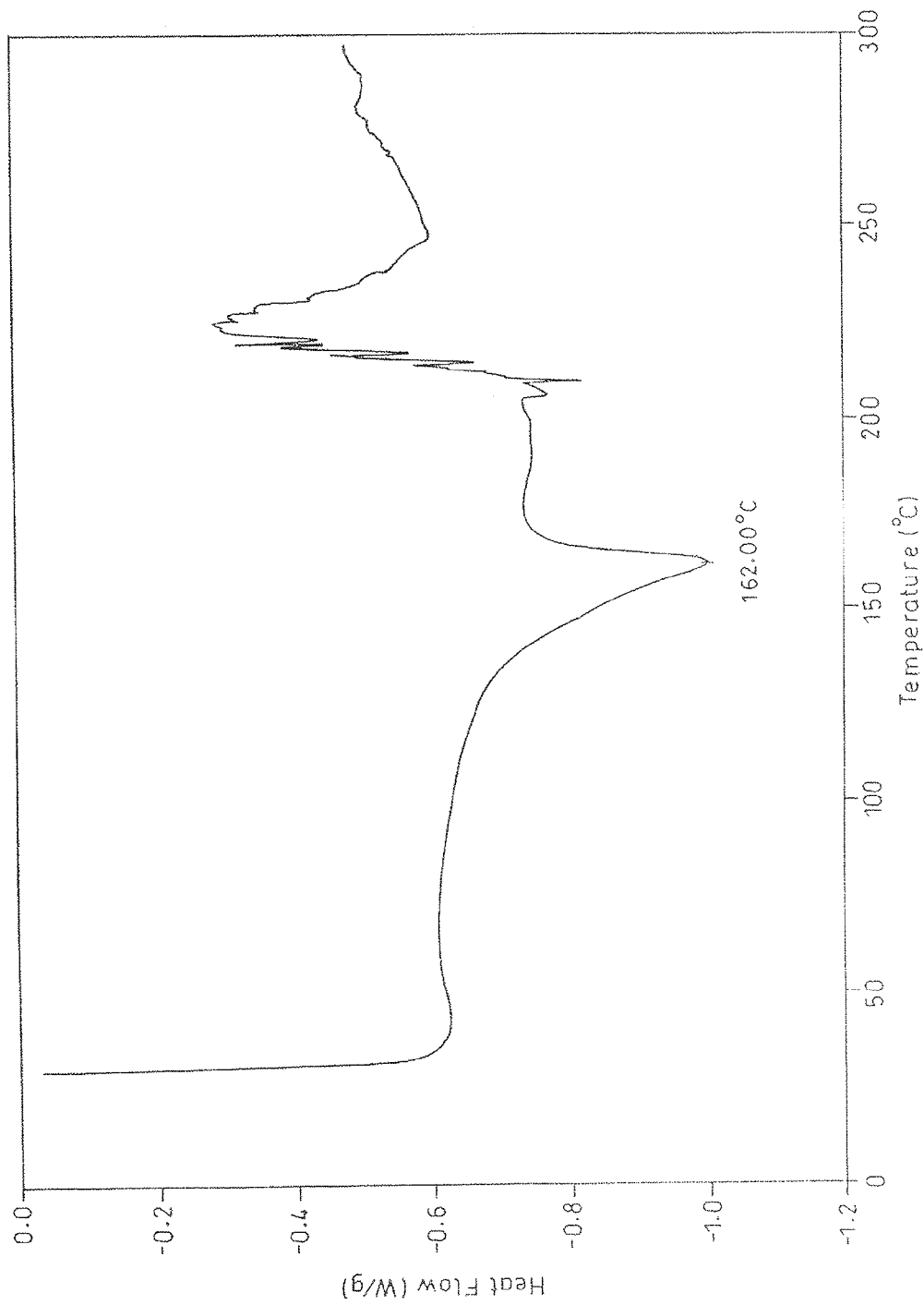
Figure 15:
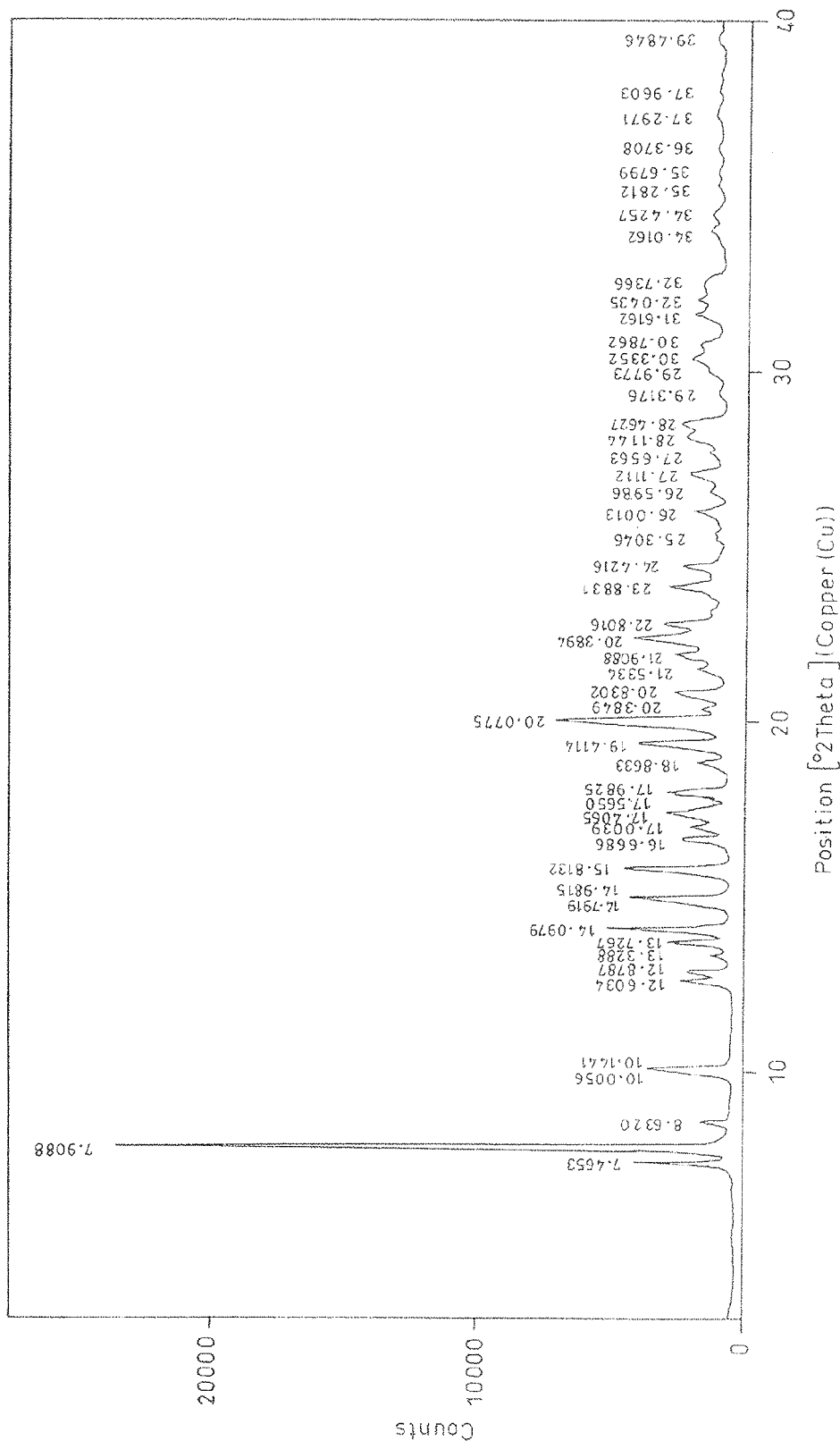
Figure 16:
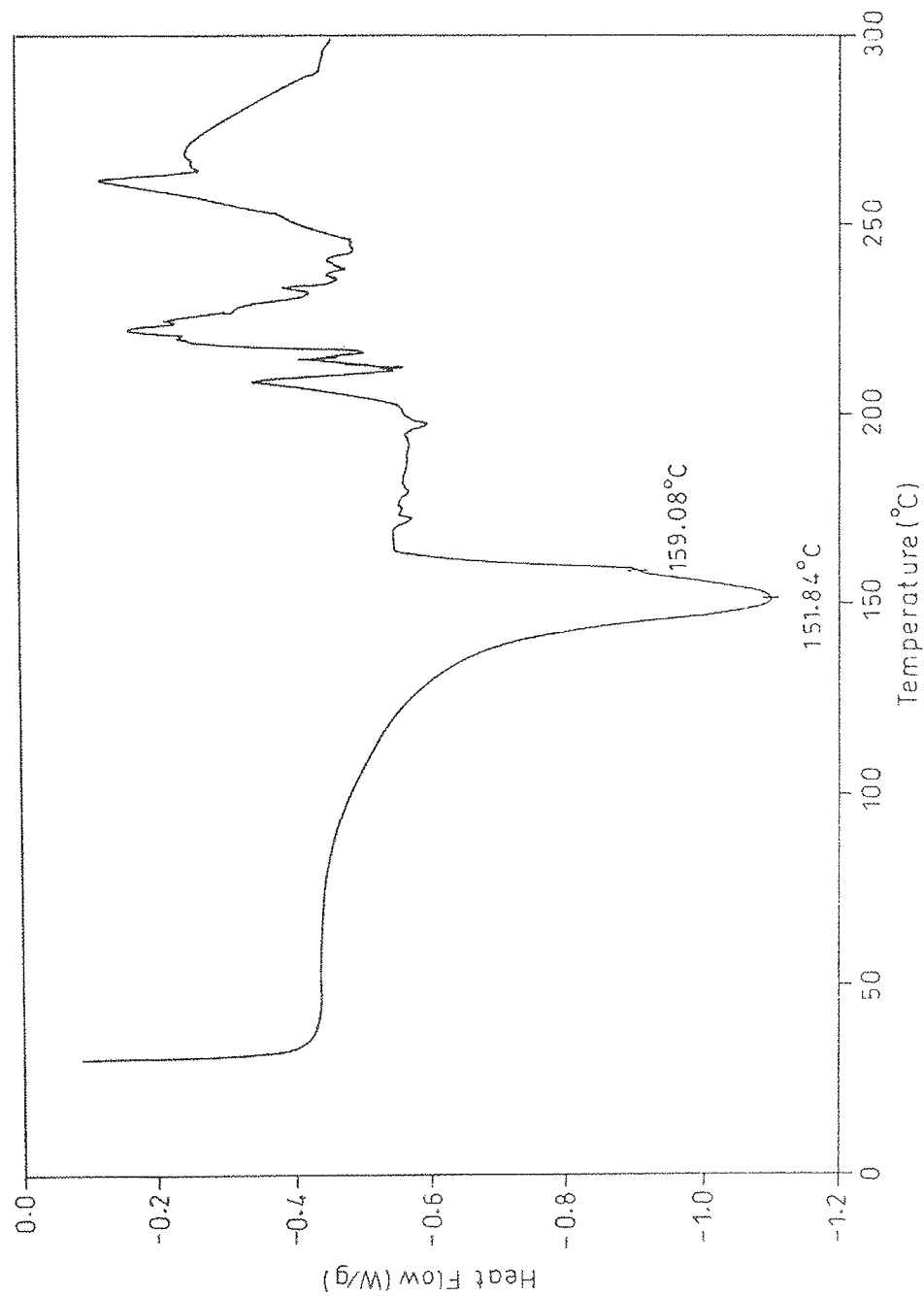
Figure 17:
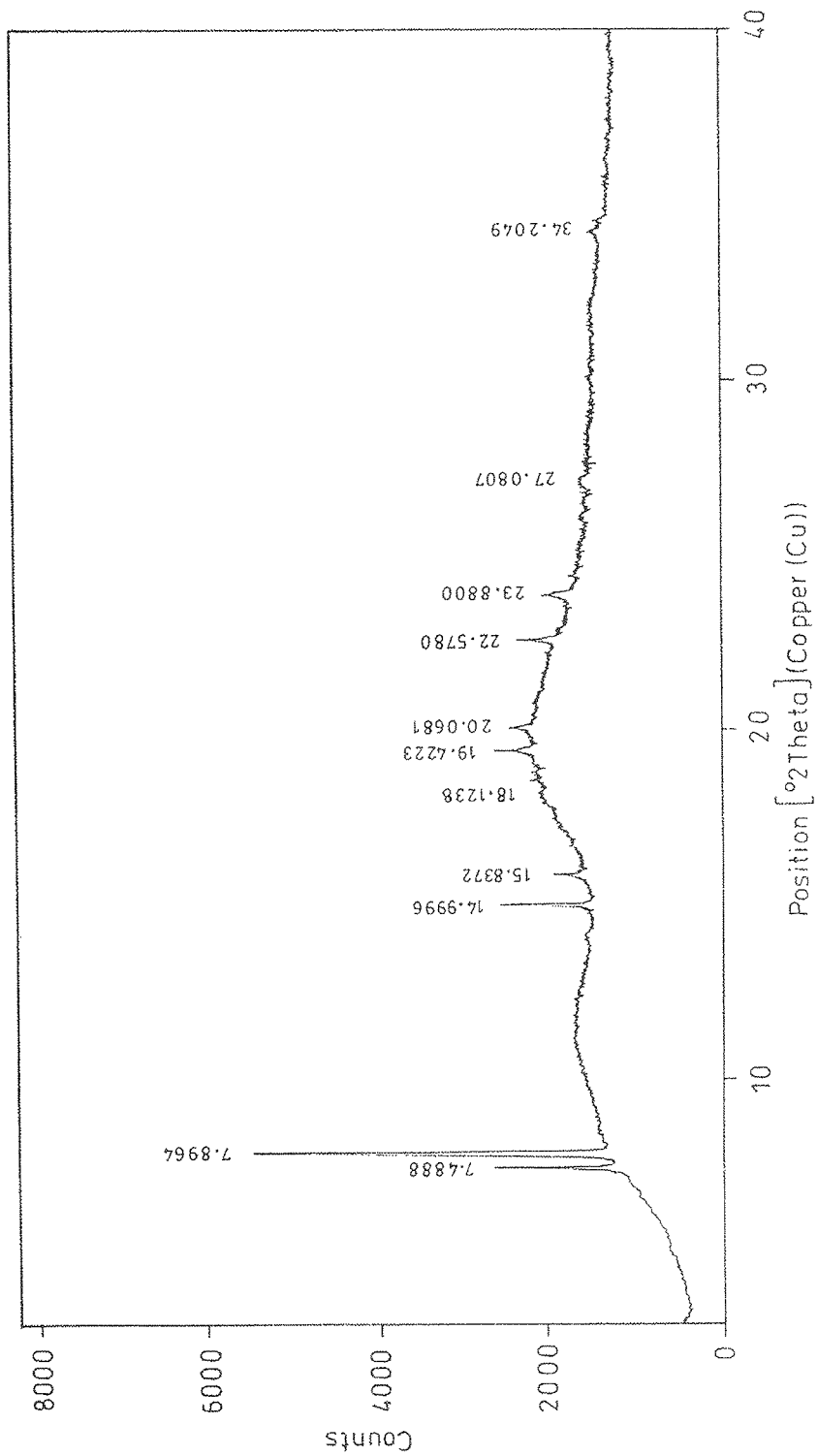
Figure 18:
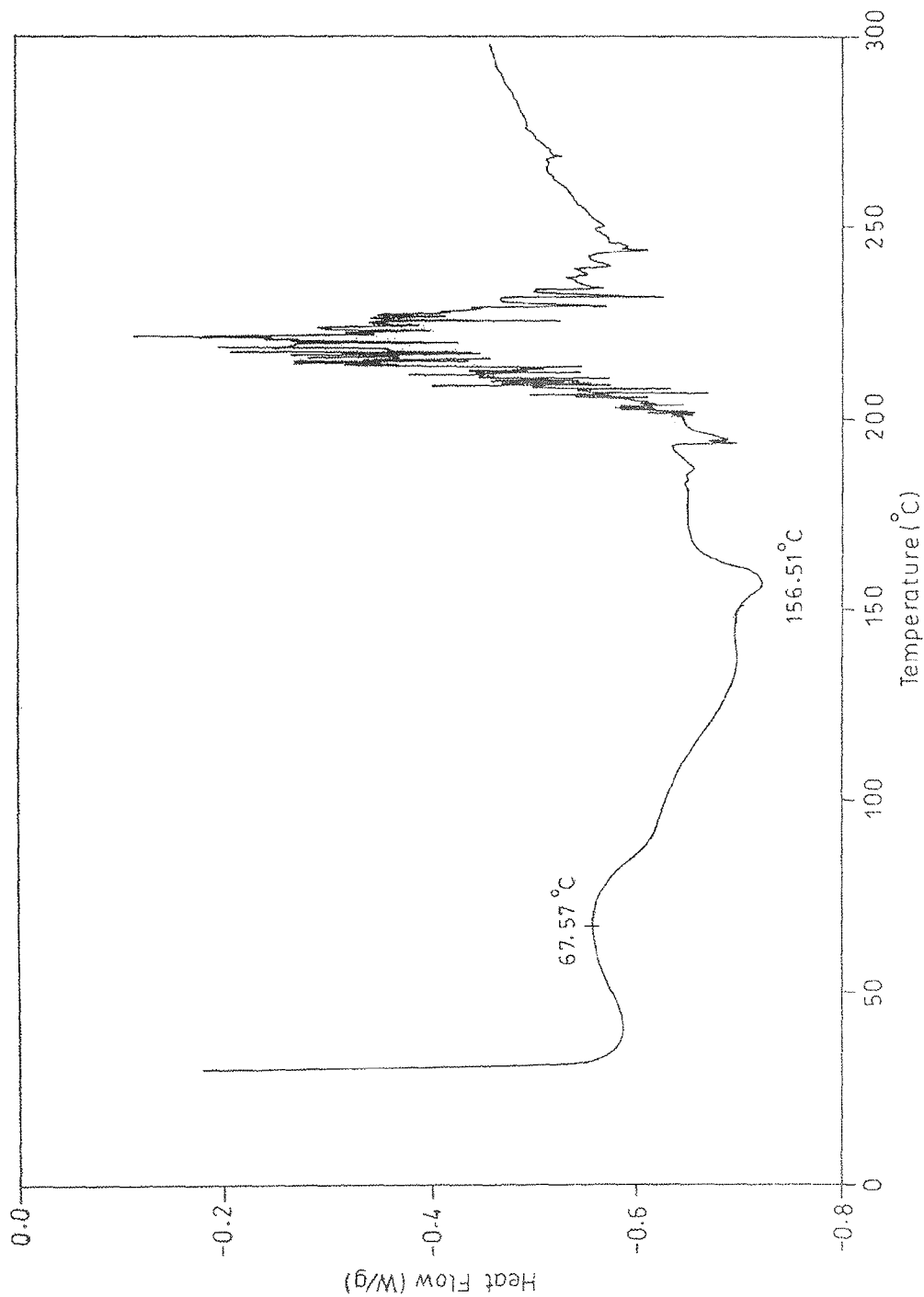
Figure 19:
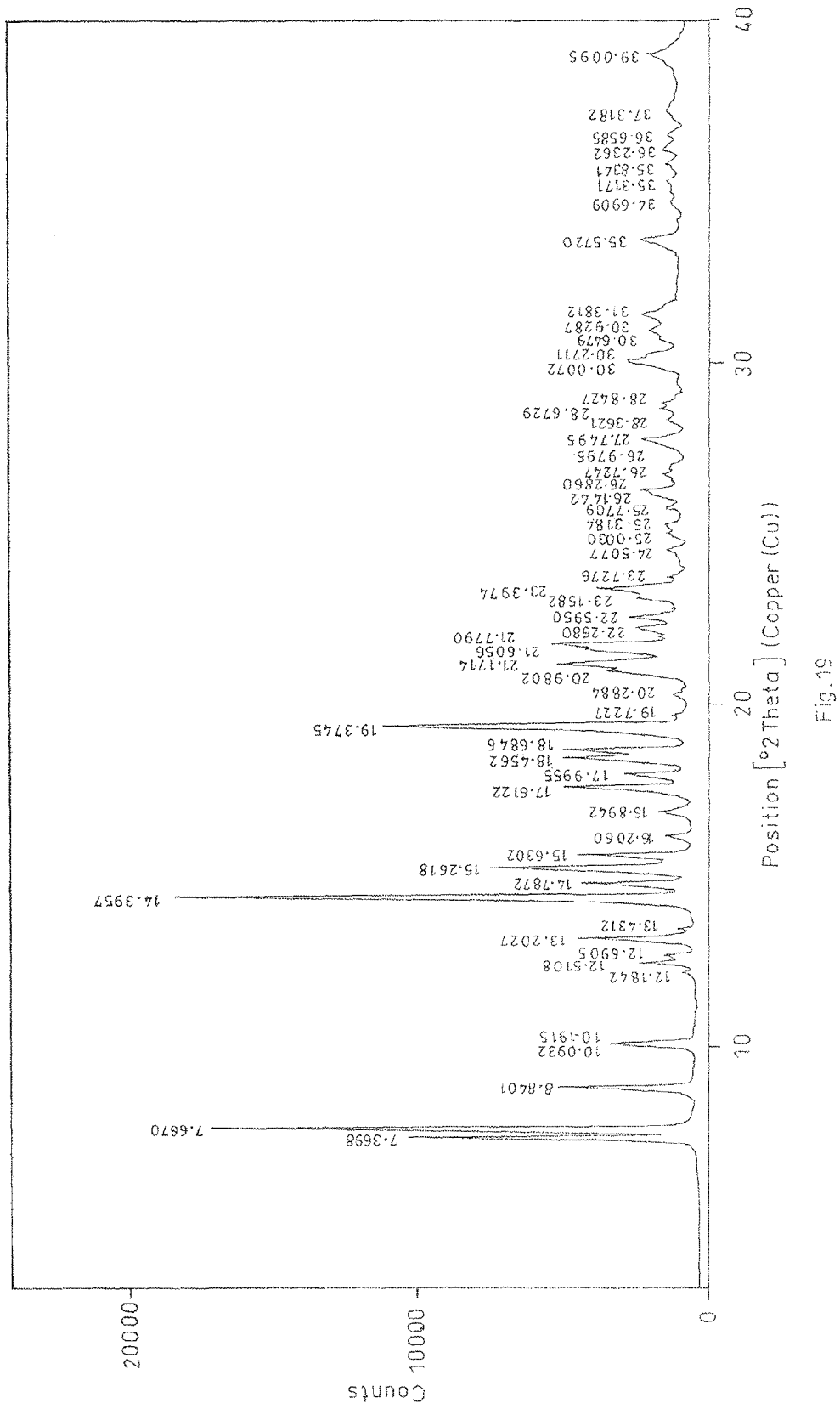
Figure 20:
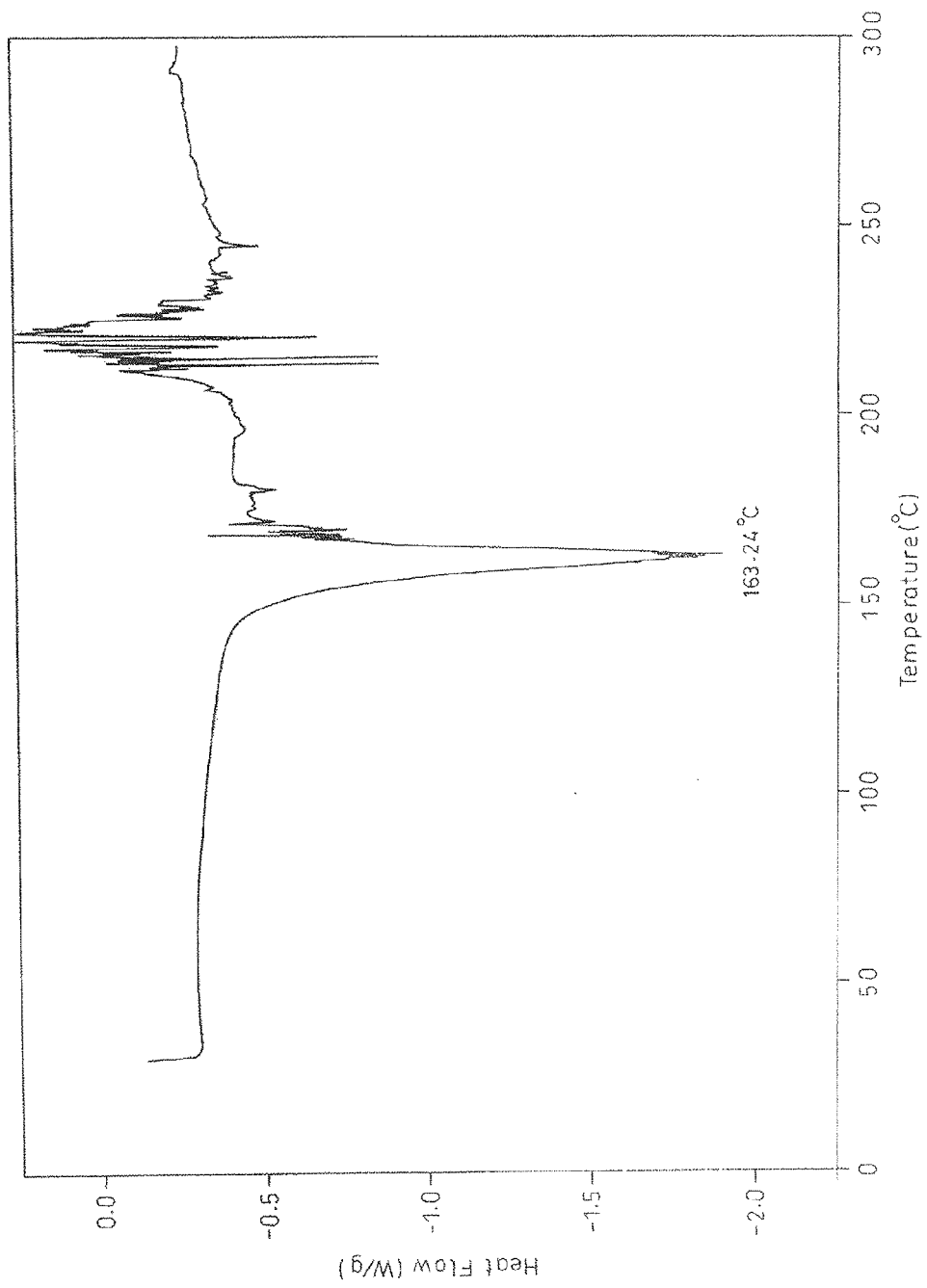
Figure 21:
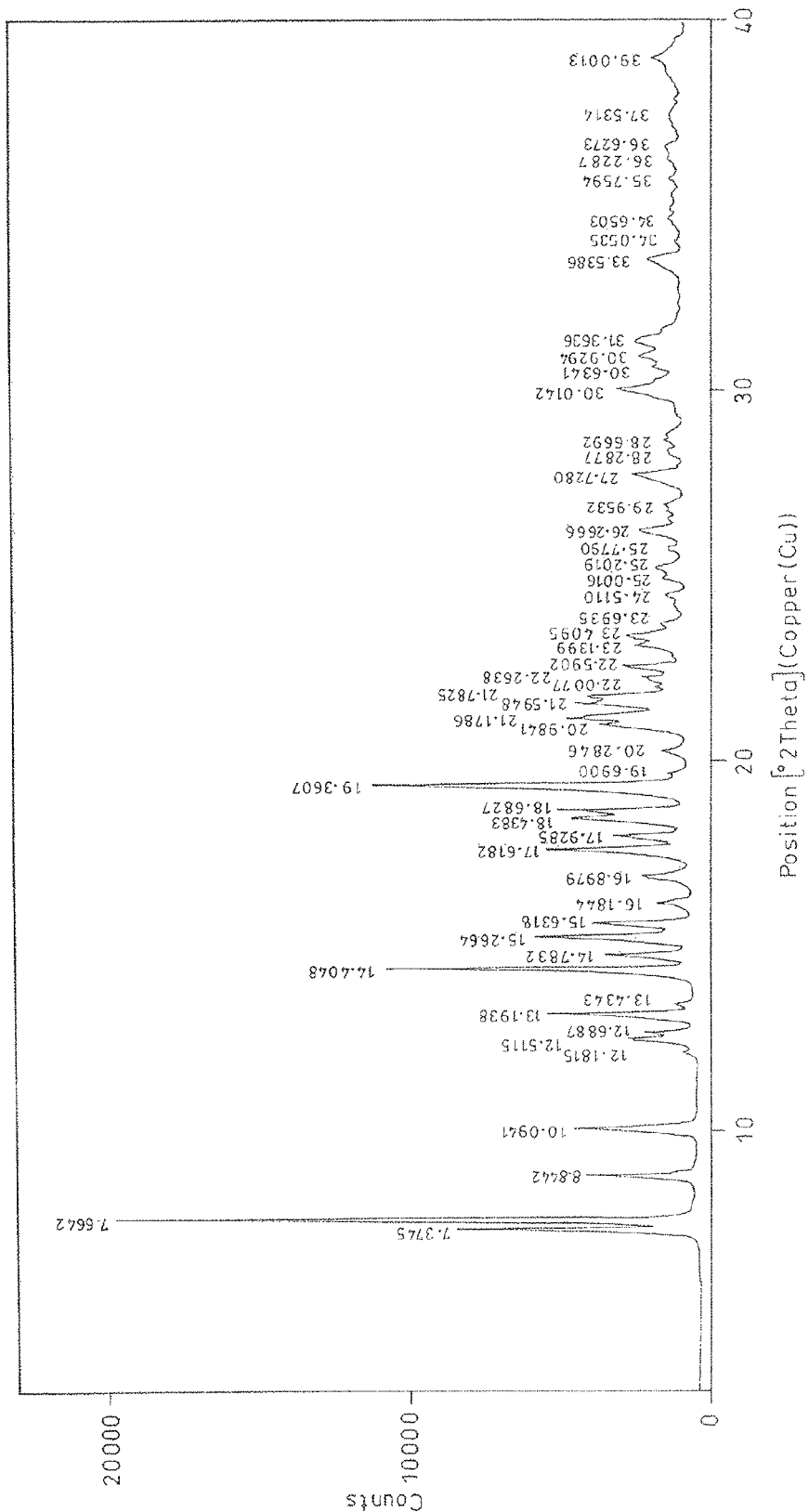
Figure 22:
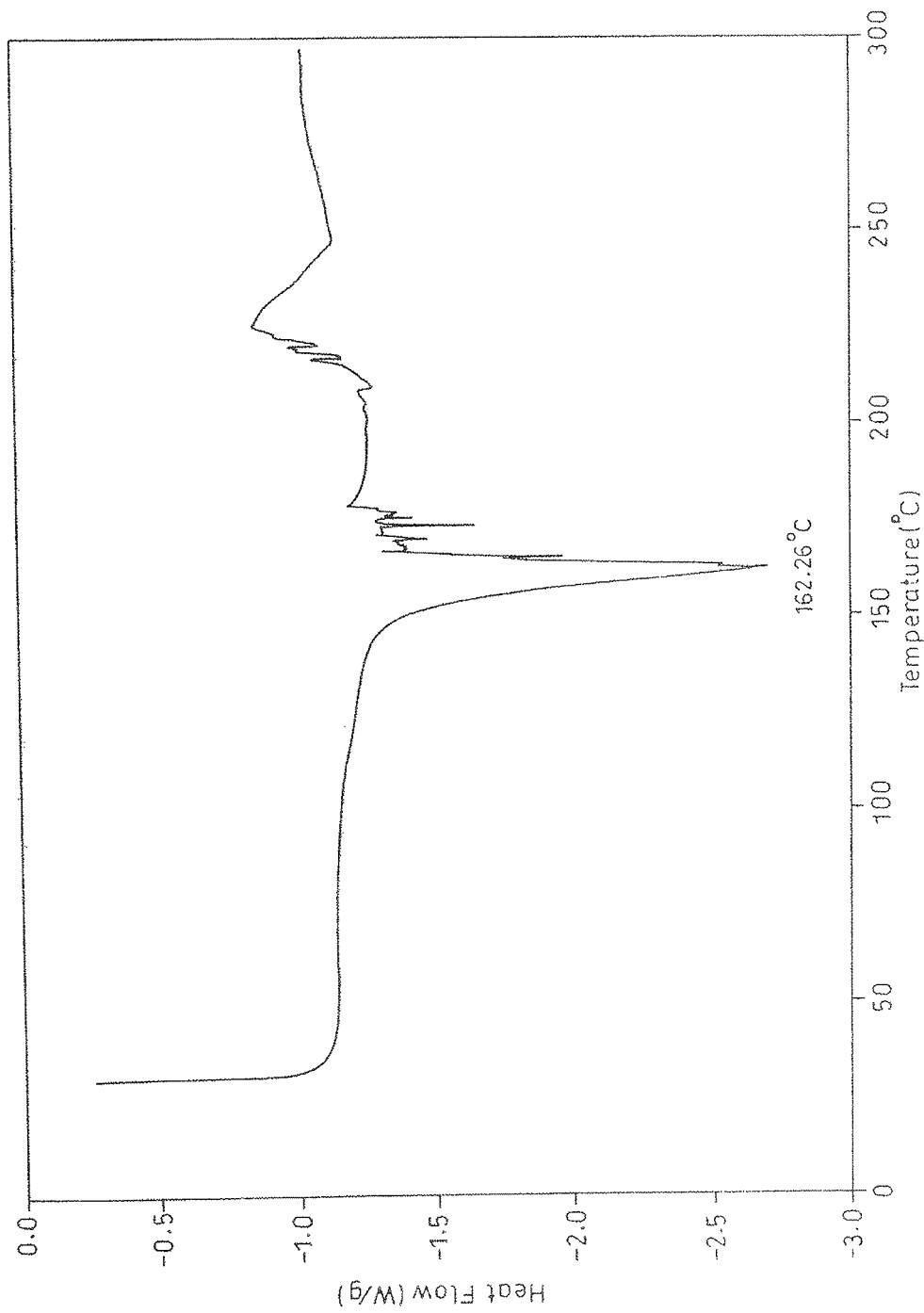
Figure 23:
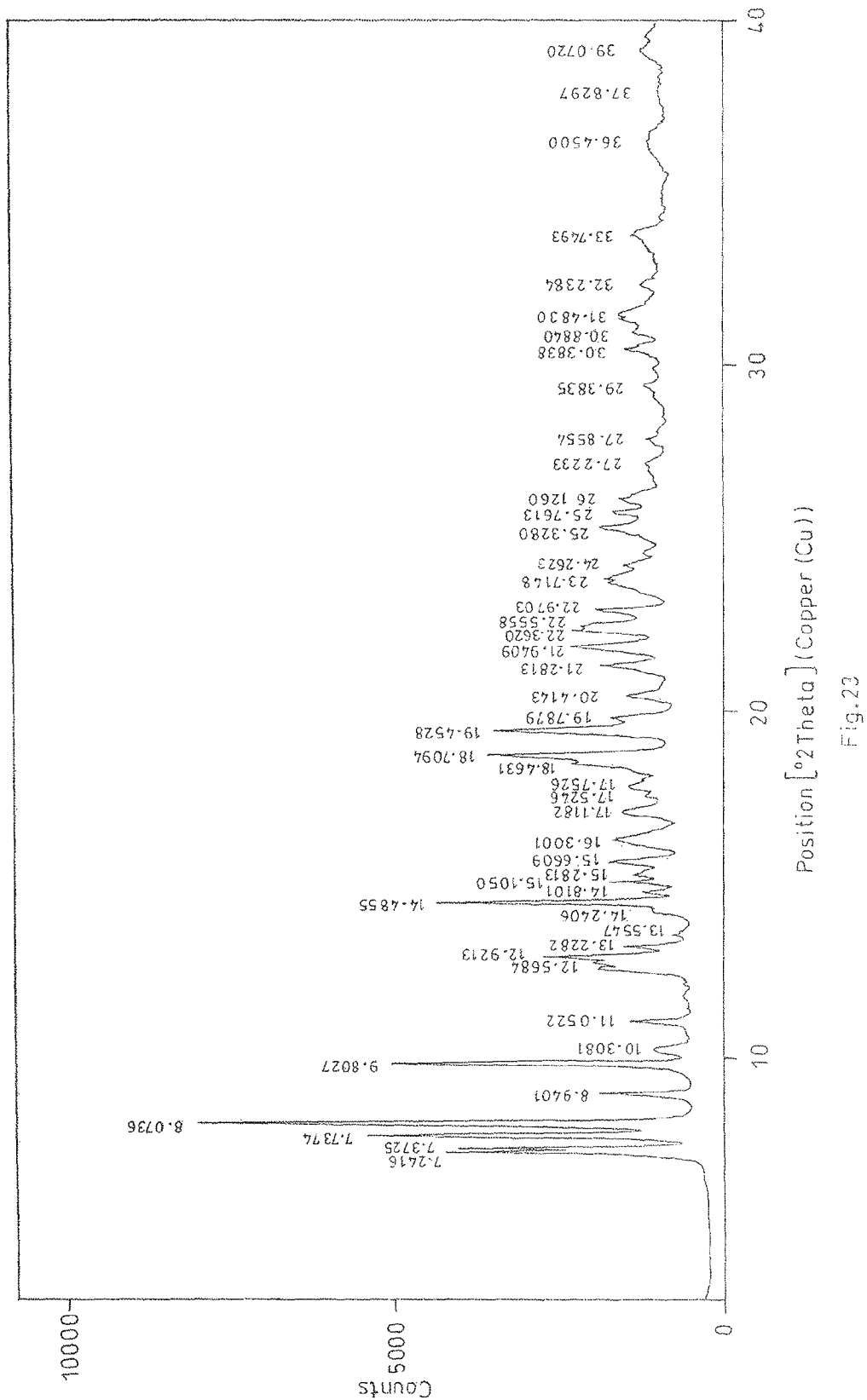
Figure 24:
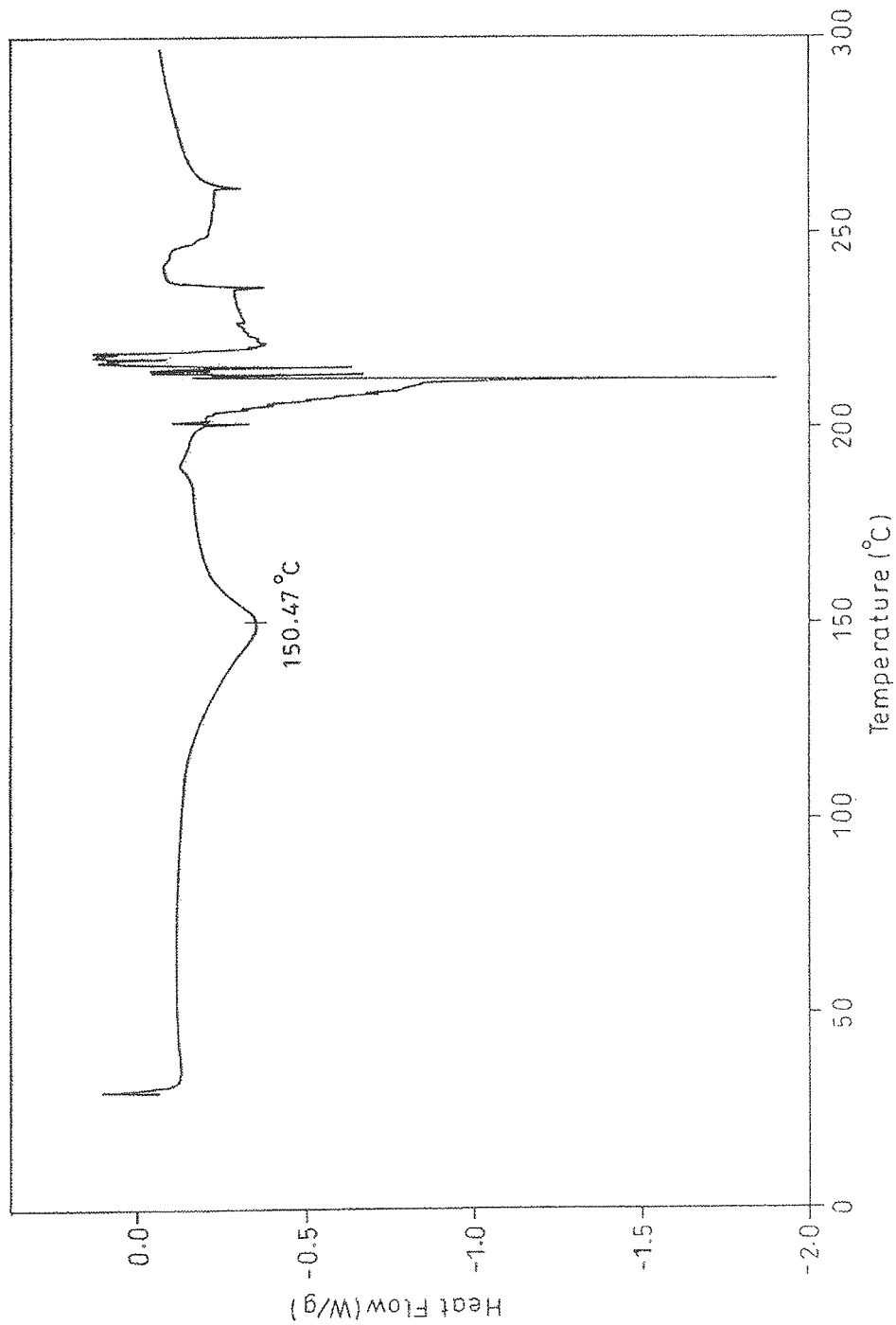
Figure 25:
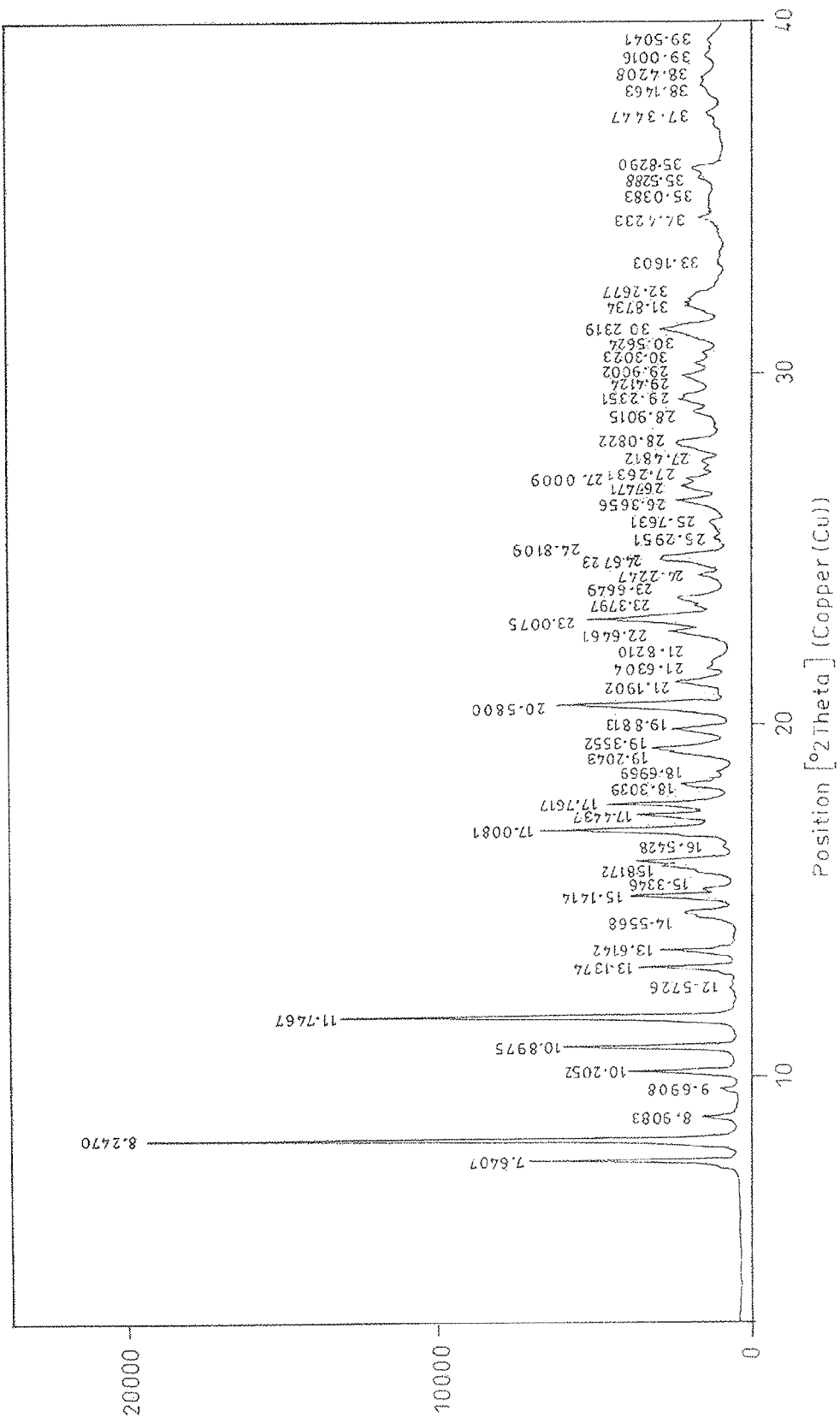
Figure 26:
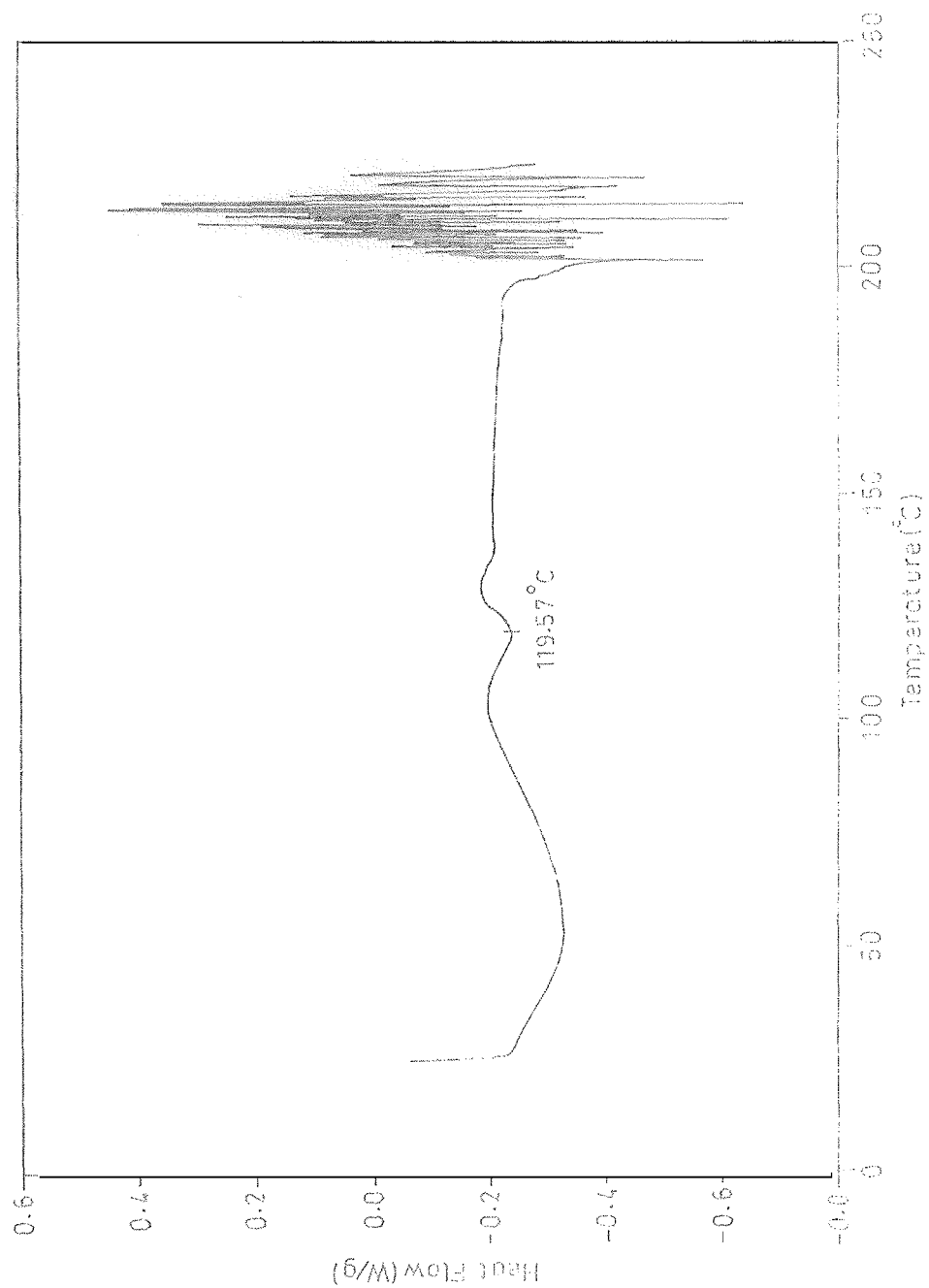

FIG. 1, which represents the X-ray (powder) diffraction pattern of the Crystalline Form-1 of Cabazitaxel of the present invention FIG. 2, which represents the Differential Scanning calorimetry (DSC) of the Crystalline Form-1 of Cabazitaxel of the present invention FIG. 3, which represents the X-ray (powder) diffraction pattern of the Crystalline Form-2 of Cabazitaxel of the present invention FIG. 4, which represents the Differential Scanning calorimetry (DSC) of the Crystalline Form-2 of Cabazitaxel of the present invention FIG. 5, which represents the X-ray (powder) diffraction pattern of the Crystalline Form-3 of Cabazitaxel of the present invention FIG. 6, which represents the Differential Scanning calorimetry (DSC) of the Crystalline Form-3 of Cabazitaxel of the present invention FIG. 7, which represents the X-ray (powder) diffraction pattern of the Crystalline Form-4 of Cabazitaxel of the present invention FIG. 8, which represents the Differential Scanning calorimetry (DSC) of the Crystalline Form-4 of Cabazitaxel of the present invention FIG. 9, which represents the X-ray (powder) diffraction pattern of the Crystalline Form-5 of Cabazitaxel of the present invention FIG. 10, which represents the Differential Scanning calorimetry (DSC) of the Crystalline Form-5 of Cabazitaxel of the present invention FIG. 11, which represents the X-ray (powder) diffraction pattern of the Crystalline Form-6 of Cabazitaxel of the present invention FIG. 12, which represents the Differential Scanning calorimetry (DSC) of the Crystalline Form-6 of Cabazitaxel of the present invention FIG. 13, which represents the X-ray (powder) diffraction pattern of the Crystalline Form-7 of Cabazitaxel of the present invention FIG. 14, which represents the Differential Scanning calorimetry (DSC) of the Crystalline Form-7 of Cabazitaxel of the present invention FIG. 15, which represents the X-ray (powder) diffraction pattern of the Crystalline Form-8 of Cabazitaxel of the present invention FIG. 16, which represents the Differential Scanning calorimetry (DSC) of the Crystalline Form-8 of Cabazitaxel of the present invention FIG. 17, which represents the X-ray (powder) diffraction pattern of the Crystalline Form-9 of Cabazitaxel of the present invention FIG. 18, which represents the Differential Scanning calorimetry (DSC) of the Crystalline Form-9 of Cabazitaxel of the present invention FIG. 19, which represents the X-ray (powder) diffraction pattern of the Crystalline Form-10 of Cabazitaxel of the present invention FIG. 20, which represents the Differential Scanning calorimetry (DSC) of the Crystalline Form-10 of Cabazitaxel of the present invention FIG. 21, which represents the X-ray (powder) diffraction pattern of the Crystalline Form-11 of Cabazitaxel of the present invention FIG. 22, which represents the Differential Scanning calorimetry (DSC) of the Crystalline Form-11 of Cabazitaxel of the present invention FIG. 23, which represents the X-ray (powder) diffraction pattern of the Crystalline Form-12 of Cabazitaxel of the present invention FIG. 24, which represents the Differential Scanning calorimetry (DSC) of the Crystalline Form-12 of Cabazitaxel of the present invention FIG. 25, which represents the X-ray (powder) diffraction pattern of the Crystalline Form-13 of Cabazitaxel of the present invention FIG. 26, which represents the Differential Scanning calorimetry (DSC) of the Crystalline Form-13 of Cabazitaxel of the present invention

DETAILED DESCRIPTION OF THE INVENTION 4-acetoxy-2α-benzoyloxy-5β-20-epoxy-1-hydroxy-7β,10β-dimethoxy-9-oxotax-11-en-13α-yl(2R,3S)-3-tert-butoxycarbonylamino-2-hydroxy-3-phenylpropionate i.e. Cabazitaxel used as starting material, may be prepared according to the method known in art such as described in U.S. Pat. No. 5,847,170.

The present invention relates to crystalline polymorphic forms of Cabazitaxel and processes for preparing them.

The present invention provides crystalline polymorphs of Cabazitaxel and process for preparing them. These polymorphs are Form-1, Form-2, Form-3, Form-4, Form-5, Form-6, Form-7, Form-8, Form-9, Form-10, Form-11, Form-12 and Form 13.

The crystalline polymorphs obtained by process of present invention, are characterized by their X-ray powder diffraction (XRPD) patterns and differential scanning calorimetry (DSC) curves.

All XRPD data reported herein were obtained using Cu Kα radiation, having the wavelength 1.541 Å and were obtained using Bruker AXS D8 advance Powder X-ray Diffractometer.

All DSC data reported herein were analyzed in hermitically sealed aluminium pan, with a blank hermitically sealed aluminium pan as the reference and were obtained using DSC (DSC $Q_{2000}$, TA Instruments USA), equipped with RCS90 cooling accessory.

Cabazitaxel crystalline Form-1 of the present invention is characterized by its XRPD having peaks at diffraction angles 2-theta of about 7.27, 8.098, 8.9288, 9.8386, 10.3719, 11.1279, 12.6872, 12.9551, 14.3024, 15.3175, and 15.7891±0.2.

Cabazitaxel crystalline Form-1 of the present invention is further characterized by its DSC curve having an endothermic peak at about 134.01° C. and 159.58° C.

Cabazitaxel crystalline Form-1 of the present invention is further characterized by its TGA curve corresponding to a weight loss of about 0.936 w/w.

Present invention provides process for the preparation of crystalline Form-1 of Cabazitaxel, comprising,
a. dissolving crude Cabazitaxel in chlorinated hydrocarbon.
b. adding aliphatic hydrocarbon solvent to the solution obtained in step (a); and
c. isolating Cabazitaxel crystalline Form-1

The present invention provides a process for the preparation of Cabazitaxel crystalline Form-1 comprising a solution of Cabazitaxel in chlorinated hydrocarbon with an anti-solvent.

The solution of Cabazitaxel is obtained by the dissolution of Cabazitaxel in suitable chlorinated hydrocarbons such as dichloromethane, dichloroethane, and the like.

The volume of the solvent, that can be used in step a) depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent. Suitable anti-solvents include but are not limited to: water; ethers such as diethyl ether, diisopropyl ether, 1,4-dioxane, dimethoxyethane, methyl tertiary-butyl ether and the like; hydrocarbons such as n-heptane, n-hexane, n-heptane, cyclohexane, benzene, toluene and the like; low boiling hydrocarbon mixtures such as petroleum ether and the like; and combination thereof.

The ratio between the solvent in solution and anti-solvent is from 1:1 to about 1:50.

The obtained Form-1 is optionally washed with an anti-solvent to reduce the organic volatile impurities content. After removal of the solvent the material was dried in vacuum oven.

Cabazitaxel crystalline Form-2 of the present invention is characterized by its XRPD having peaks at diffraction angles 2-theta of about 3.9477, 6.9328, 7.8516, 10.1685, 10.7552, 11.6174, 12.1755, 12.8255, 13.5716, 14.0264, 15.1085, 17.2533 and 18.1414±0.2.

Cabazitaxel crystalline Form-2 of the present invention is further characterized by its DSC curve having endothermic peaks at about 68.5, 114.59 and 174° C.

Cabazitaxel crystalline Form-2 of the present invention is further characterized by its TGA curve corresponding to a weight loss of about 5.88 w/w. It has water content of about 2.7% w/w by the KF method.

The present invention provides a process for the preparation of Cabazitaxel crystalline Form-2 comprising a solution of Cabazitaxel in dimethyl sulfoxide at suitable temperature.

The solution of Cabazitaxel is obtained by the dissolution of Cabazitaxel in dimethyl sulfoxide.

The volume of the solvent, that can be used in step a) depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as water.

The ratio between the solvent in solution and anti-solvent is from 1:1 to about 1:50.

The obtained Form-2 is optionally washed with an anti-solvent to reduce the organic volatile impurities content. After removal of the solvent the material was dried in vacuum Oven.

Cabazitaxel crystalline Form-3 of the present invention is characterized by its XRPD having peaks at diffraction angles 2-theta of about 4.2517, 6.9143, 7.5307, 8.5018, 8.6671, 10.0963, 11.016, 11.7729, 12.2981, 12.655, 13.2716, 13.3755, 13.8385, 14.3319, 15.1075, 15.5934±0.2.

Cabazitaxel crystalline Form-3 of the present invention is further characterized by its DSC curve having an endothermic peak at about 71.59° C.

Cabazitaxel crystalline Form-3 of the present invention is further characterized by its TGA curve corresponding to a weight loss of about 1.44 w/w. It has water content of about 4.10% w/w by the KF method.

The present invention provides a process for the preparation of Cabazitaxel crystalline Form-3 comprising a solution of Cabazitaxel in acetonitrile at suitable temperature.

The solution of Cabazitaxel is obtained by the dissolution of Cabazitaxel in acetonitrile.

The volume of the solvent, that can be used in depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as water.

The ratio between the solvent in solution and anti-solvent is from 1:1 to about 1:50.

The obtained Form-3 is optionally washed with an anti-solvent to reduce the organic volatile impurities content. After removal of the solvent the material was dried in vacuum Oven.

Cabazitaxel crystalline Form-4 of the present invention is characterized by its XRPD having peaks at diffraction angles 2-theta of about 6.9147, 7.9157, 10.1788, 10.7274, 12.2545, 13.9828, 15.1051, 17.2041, 18.1419, 19.7907, 21.5114, 23.1898, 24.6259, 25.3476 and 35.589±0.2.

Cabazitaxel crystalline Form-4 of the present invention is further characterized by its DSC curve having endothermic peaks at about 45.35 and 124.92° C.

Cabazitaxel crystalline Form-4 of the present invention is further characterized by its TGA curve corresponding to a weight loss of about 4.82 w/w. It has water content of about 2.09% w/w by the KF method.

The present invention provides a process for the preparation of Cabazitaxel crystalline Form-4 comprising a solution of Cabazitaxel in dimethylsulfoxide at suitable temperature.

The solution of Cabazitaxel is obtained by the dissolution of Cabazitaxel in dimethylsulfoxide.

The volume of the solvent, that can be used in depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by reverse addition to the anti-solvent such as water.

The ratio between the solvent in solution and anti-solvent is from 1:1 to about 1:50.

The obtained Form-4 is optionally washed with an anti-solvent to reduce the organic volatile impurities content. After removal of the solvent the material was dried in vacuum Oven.

Cabazitaxel crystalline Form-5 of the present invention is characterized by its XRPD having peaks at diffraction angles 2-theta of about 4.2714, 6.9202, 7.5398, 8.627, 10.1116, 11.056, 11.839, 12.299, 12.6699, 13.4006, 13.835, 14.3439, 15.0177, 15.6442, 16.4676, 17.1655, 18.2157, 18.7109, 20.1774, 20.348, 21.1891, 21.6012, 22.2294, 22.9478, 24.6888, 25.4707, 25.9011, 26.8967, 27.7873, 29.5789, 32.2693, 34.5618, 35.4515, 36.6906 and 38.1087±0.2.

Cabazitaxel crystalline Form-5 of the present invention is further characterized by its DSC curve having endothermic peaks at about 56.29 and 145.27° C.

Cabazitaxel crystalline Form-5 of the present invention is further characterized by its TGA curve corresponding to a weight loss of about 0.97 w/w. It has water content of about 3.24% w/w by the KF method.

The present invention provides a process for the preparation of Cabazitaxel crystalline Form-5 comprising a solution of Cabazitaxel in methanol at suitable temperature.

The solution of Cabazitaxel is obtained by the dissolution of Cabazitaxel in methanol.

The volume of the solvent, that can be used in depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as water.

The ratio between the solvent in solution and anti-solvent is from 1:1 to about 1:50.

The obtained Form-5 is optionally washed with an anti-solvent to reduce the organic volatile impurities content. After removal of the solvent the material was dried in vacuum Oven.

Cabazitaxel crystalline Form-6 of the present invention is characterized by its XRPD having peaks at diffraction angles 2-theta of about 7.5382, 7.8933, 8.5705, 9.0313, 9.9955, 12.53567, 12.7543, 13.1642, 13.8096, 14.1239, 14.9894, 15.1341, 15.5073, 15.8243, 15.9533, 16.6157, 16.8378, 17.3433, 17.8146, 18.7843, 19.6295, 20.0721, 20.272, 20.6837, 21.6467, 22.0733, 22.4547, 22.8002, 23.352, 23.8517, 24.4177, 25.2362, 25.9305, 26.3936, 26.9242, 27.4422, 27.8523, 28.2344, 28.8554, 30.1018, 30.9761, 31.3884, 32.409, 33.0368, 34.1981, 34.9906, 36.1324, 36.5453, 37.1655, 37.8404 and 38.3193±0.2.

Cabazitaxel crystalline Form-6 of the present invention is further characterized by its DSC curve having an endothermic peak at about 157.26° C.

Cabazitaxel crystalline Form-6 of the present invention is further characterized by its TGA curve corresponding to a weight loss of about 4.0 w/w.

The present invention provides a process for the preparation of Cabazitaxel crystalline Form-6 by deprotecting the side chain of 4α-acetoxy-2α-benzoyloxy-5β,20-epoxy-1β, 13α-dihydroxy-7β,10β-dimethoxy-9-oxo-11-taxen-13α-yl-(2R,4S,5S)-3-tert-butoxycarbonyl-2-(4-methoxy phenyl)-4-phenyl-1,3-oxazolidine-5-carboxylate of the formula II in ethyl acetate and a solution of 0.25 N HCl in ethylacetate to obtain the crude Cabazitaxel of formula (I).

Formula I

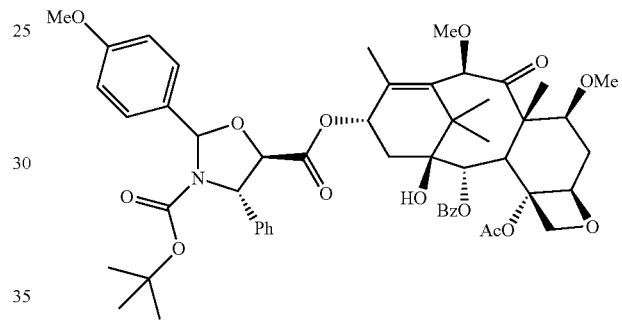

The solution of Cabazitaxel is obtained by the dissolution of Cabazitaxel in Toluene.

The volume of the solvent, that can be used in depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by keeping the solution in refrigerator at 0-5° C.

The obtained Form-6 is filtered and washed with an anti-solvent to reduce the organic volatile impurities content. After removal of the solvent the material was dried in vacuum Oven.

Cabazitaxel crystalline Form-7 of the present invention is characterized by its XRPD having peaks at diffraction angles 2-theta of about 5.1654, 6.0558, 7.5462, 7.7852, 8.8713, 9.5395, 10.1166, 10.3287, 10.3287, 10.7561, 11.3142, 11.6744, 11.7668, 12.0871, 12.5438, 12.7839, 13.0253, 13.3688, 14.147, 14.4314, 15.2768, 15.4254, 15.7276, 16.0658, 16.7552, 17.1127, 17.633, 18.0978, 18.5174, 18.9323, 19.6057, 20.309, 21.0129, 21.3404, 21.8444, 22.3403, 22.7858, 23.4707, 24.0622, 24.479, 25.1489, 25.6754, 26.632, 27.1126, 27.884, 28.8493, 30.3359, 30.7151, 31.6619, 32.6055, 33.4331, 35.9047, 36.7957, 37.5168 and 38.4523±0.2.

Cabazitaxel crystalline Form-7 of the present invention is further characterized by its DSC curve having an endothermic peak at about 162° C.

Cabazitaxel crystalline Form-7 of the present invention is further characterized by its TGA curve corresponding to a weight loss of about 1.902 w/w.

The present invention provides a process for the preparation of Cabazitaxel crystalline Form-7 comprising a solution of Cabazitaxel in tetrahydrofuran at suitable temperature.

The solution of Cabazitaxel is obtained by the dissolution of Cabazitaxel in tetrahydrofuran.

The volume of the solvent, that can be used in depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as n-hexane.

The ratio between the solvent in solution and anti-solvent is from 1:1 to about 1:50.

The obtained Form-7 is optionally washed with an anti-solvent to reduce the organic volatile impurities content. After removal of the solvent the material was dried in vacuum Oven.

Cabazitaxel crystalline Form-8 of the present invention is characterized by its XRPD having peaks at diffraction angles 2-theta of about 7.4653, 7.9088, 8.632, 10.0056, 10.1441, 12.6034, 12.8787, 13.3288, 13.7267, 14.0979, 14.7919, 14.9815, 15.8132, 16.6686, 17.0039, 17.4065, 17.565, 17.9825, 18.8633, 19.4114, 20.0775, 20.3849, 20.8302, 21.5334, 21.9088, 22.3894, 22.8016, 23.8831, 24.4216, 25.3046, 26.0013, 26.5986, 27.1112, 27.6563, 28.1144, 28.4627, 29.3176, 29.9773, 30.3352, 30.7862, 31.6162, 32.0435, 32.7366, 34.0162, 34.4257, 35.2812, 35.6799, 36.3708, 37.2971, 37.9603 and 39.4846±0.2.

Cabazitaxel crystalline Form-8 of the present invention is further characterized by its DSC curve having an endothermic peak at about 151.84 and 159.08° C.

Cabazitaxel crystalline Form-8 of the present invention is further characterized by its TGA curve corresponding to a weight loss of about 7.126 w/w.

The present invention provides a process for the preparation of Cabazitaxel crystalline Form-8 comprising a solution of Cabazitaxel in Ethyl acetate at suitable temperature.

The solution of Cabazitaxel is obtained by the dissolution of Cabazitaxel in Ethyl acetate.

The volume of the solvent, that can be used depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as n-hexane.

The ratio between the solvent in solution and anti-solvent is from 1:1 to about 1:50. The obtained Form-8 is optionally washed with an anti-solvent to reduce the organic volatile impurities content.

The obtained Form-8 is optionally washed with an anti-solvent to reduce the organic volatile impurities content. After removal of the solvent the material was dried in vacuum Oven.

Cabazitaxel crystalline Form-9 of the present invention is characterized by its XRPD having peaks at diffraction angles 2-theta of about 7.4888, 7.8964, 14.9996, 15.8372, 18.1238, 19.4223, 20.0681, 22.578, 23.88, 27.0807 and 34.2049±0.2.

Cabazitaxel crystalline Form-9 of the present invention is further characterized by its DSC curve having an endothermic peak at about 156.51° C.

Cabazitaxel crystalline Form-9 of the present invention is further characterized by its TGA curve corresponding to a weight loss of about 3.31 w/w.

The present invention provides a process for the preparation of Cabazitaxel crystalline Form-9 comprising a solution of Cabazitaxel in Ethyl acetate at suitable temperature.

The solution of Cabazitaxel is obtained by the dissolution of Cabazitaxel in Ethyl acetate.

The volume of the solvent, that can be used depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by distillation of the solution at suitable temperature under vacuum.

The distillation of the solvent may be carried out by heating the solution from 30-100° C.

Cabazitaxel crystalline Form-10 of the present invention is characterized by its XRPD having peaks at diffraction angles 2-theta of 7.3698, 7.667, 8.8401, 10.0932, 10.1915, 12.1842, 12.5108, 12.6905, 13.2027, 13.4312, 14.3957, 14.7872, 15.2618, 15.6302, 16.206, 16.8942, 17.6122, 17.9955, 18.4562, 18.6846, 19.3745, 19.7227, 20.2884, 20.9802, 21.1714, 21.6056, 21.779, 22.268, 22.595, 23.1582, 23.3974, 23.7276, 24.5077, 25.003, 25.3184, 25.7709, 26.1442, 26.286, 26.7247, 26.9795, 27.7495, 28.3621, 28.6729, 28.8427, 30.0072, 30.2711, 30.6479, 30.9287, 31.3812, 33.572, 34.6909, 35.3171, 35.8341, 36.2362, 36.6585, 37.3182, 39.0095±0.2.

Cabazitaxel crystalline Form-10 of the present invention is further characterized by its DSC curve having an endothermic peak at about 163.24° C.

Cabazitaxel crystalline Form-10 of the present invention is further characterized by its TGA curve corresponding to a weight loss of about 1.39 w/w.

The present invention provides a process for the preparation of Cabazitaxel crystalline Form-10 comprising a solution of Cabazitaxel in tetrahydrofuran at suitable temperature.

The solution of Cabazitaxel is obtained by the dissolution of Cabazitaxel in Tetrahydrofuran.

The volume of the solvent, that can be used depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as Methyl tert-butyl ether.

The ratio between the solvent in solution and anti-solvent is from 1:1 to about 1:50.

The obtained Form-10 is optionally washed with an anti-solvent to reduce the organic volatile impurities content.

Cabazitaxel crystalline Form-11 of the present invention is characterized by its XRPD having peaks at diffraction angles 2-theta of 7.3745, 7.6642, 8.8442, 10.0941, 12.1815, 12.5115, 12.6887, 13.1938, 13.4343, 14.4048, 14.7832, 15.2664, 15.6318, 16.1844, 16.8979, 17.6182, 17.9285, 17.9944, 18.4383, 18.6827, 19.3607, 19.69, 20.2846, 20.9841, 21.1786, 21.2743, 21.5948, 21.7825, 22.0077, 22.2638, 22.5902, 23.1399, 23.4095, 23.6935, 24.511, 25.0016, 25.2019, 25.779, 26.2666, 26.9532, 27.728, 28.2877, 28.6692, 30.0142, 30.6341, 30.9294, 31.3636, 33.5386, 34.0535, 34.6503, 35.7594, 36.2287, 36.6173, 37.5314 and 39.0013±0.2.

Cabazitaxel crystalline Form-11 of the present invention is further characterized by its DSC curve having an endothermic peak at about 162.26° C.

Cabazitaxel crystalline Form-11 of the present invention is further characterized by its TGA curve corresponding to a weight loss of about 1.91 w/w.

The present invention provides a process for the preparation of Cabazitaxel crystalline Form-11 comprising a solution of Cabazitaxel in Dichloromethane at suitable temperature.

The solution of Cabazitaxel is obtained by the dissolution of Cabazitaxel in Dichloromethane.

The volume of the solvent, that can be used in depends on the polarity and the solubilizing capacity of the solvent and typically can be employed in the range of between 2 to 100 times by volume per gram of Cabazitaxel.

The solution of Cabazitaxel in suitable solvent may be obtained at ambient temperature or heated the solution from 30-100° C.

Cabazitaxel is crystallized from the solution by combining with an anti-solvent such as Methyl tert-butyl ether.

The ratio between the solvent in solution and anti-solvent is from 1:1 to about 1:50.

The obtained Form-11 is optionally washed with an anti-solvent to reduce the organic volatile impurities content.

Cabazitaxel crystalline Form-12 of the present invention is characterized by its XRPD having peaks at diffraction angles 2-theta of 7.2416, 7.3725, 7.7374, 8.0736, 8.9401, 9.8027, 10.3081, 11.0522, 12.5684, 12.9213, 13.2282, 13.5547, 14.2406, 14.4855, 14.8101, 15.105, 15.2813, 15.6609, 16.3001, 17.1182, 17.5246, 17.7526, 18.4631, 18.7094, 19.4528, 19.7879, 20.4143, 21.2813, 21.9409, 22.362, 22.5558, 22.9703, 23.7148, 24.2623, 25.328, 25.7613, 26.126, 27.2233, 27.8554, 29.3835, 30.3838, 30.884, 31.483, 32.2384, 33.7493, 36.45, 37.8297 and 39.072±0.2.

Cabazitaxel crystalline Form-12 of the present invention is further characterized by its DSC curve having an endothermic peak at about 150.47° C.

Cabazitaxel crystalline Form-12 of the present invention is further characterized by its TGA curve corresponding to a weight loss of about 4.03 w/w.

The present invention provides a process for the preparation of Cabazitaxel crystalline Form-12 comprising a solution of Cabazitaxel in Dichloromethane at suitable temperature.

The solution of Cabazitaxel is obtained by the dissolution of Cabazitaxel in Dichloromethane.

The volume of the solvent, that can be used in depends on the polarity and the solubilizing capacity of the solvent and typically can be employed in the range of between 2 to 100 times by volume per gram of Cabazitaxel.

Cabazitaxel is crystallized from the solution by keeping the solution at suitable temperature for 2 days.

The crystallized material was and filtered to obtain Form-12 of Cabazitaxel. After removal of the solvent the material was dried in vacuum Oven.

Cabazitaxel crystalline Form-13 of the present invention is characterized by its XRPD having peaks at diffraction angles 2-theta of 7.6407, 8.2470, 8.9083, 9.6908, 10.2052, 10.8975, 11.7467, 12.5726, 13.1374, 13.6142, 14.5568, 14.7306, 15.1414, 15.3346, 15.8172, 15.9783, 16.1685, 16.5428, 17.0081, 17.4437, 17.7617, 18.3039, 18.6969, 19.2043, 19.3552, 19.8813, 20.5800, 21.1902, 21.6304, 21.8210, 22.6461, 23.0075, 23.3798, 23.6649, 24.227, 24.6723, 24.8109, 25.2951, 25.7631, 26.3656, 26.7471, 27.009, 27.2631, 27.4812, 28.0822, 28.9015, 29.2351, 29.4124, 29.9002 and 30.3023±0.2.

Cabazitaxel crystalline Form-13 of the present invention is further characterized by its DSC curve having an endothermic peak at about 119.57° C.

Cabazitaxel crystalline Form-13 of the present invention is further characterized by its TGA curve corresponding to a weight loss of about 3.058 w/w.

The present invention provides a process for the preparation of Cabazitaxel crystalline Form-13 comprising a solution of Cabazitaxel in acetonitrile at suitable temperature.

The solution of Cabazitaxel is obtained by the dissolution of Cabazitaxel in acetonitrile.

The volume of the solvent, that can be used in depends on the polarity and the solubilizing capacity of the solvent and typically can be employed in the range of between 2 to 100 times by volume per gram of Cabazitaxel.

Cabazitaxel is crystallized from the solution by keeping the solution at suitable temperature for 2 hours. After removal of the solvent the material was dried in vacuum Oven.

The resulting forms of Cabazitaxel may be formulated into ordinary dosage forms such as, for example, tablets, capsules, pills, solutions, etc. In these cases, the medicaments can be prepared by conventional methods with conventional pharmaceutical excipients.

Further, the crystalline Cabazitaxel described herein can be used in a method for treatment of hormone-refractory metastatic prostate cancer. The method of treatment includes administering to a mammal in need of treatment a dosage form that includes a therapeutically effective amount of the amorphous form of Cabazitaxel.

The methods for the preparation of the Crystalline Forms of Cabazitaxel of the present invention may be illustrated by way of the following examples, which is no way should be construed as limiting the scope of the invention.

EXAMPLES

Example-1

Charged Cabazitaxel (2.0 g) and DCM (10 mL) and stirred to dissolve the solid. Charged the solution into n-Hexane (50 mL) under stirring at 20-25° C. Reaction mixture was stirred for 30 min at 20-25° C. Filter the obtained solid and washed with n-Hexane (20 mL). Material was dried for 30 min at room temperature and 50-55° C. for 6 h under 0-10 mbar to get Form-1 of Cabazitaxel.

DSC –134.01° C. and 159.58° C.
TGA –0.936 (up to 105° C.)
Purity –92.42%

Example-2

Charged 140 g Cabazitaxel in 700 ml pre-distilled dichloromethane and stirred for 15-20 min to dissolve the solid material. The solution was filtered through micron filter paper and filtrate is heated to distill the solvent under vacuum below 40° C. to get the solid material. The solid material is dried under vacuum for 1 hour. Charged 420 ml of pre-distilled Dichloromethane to the solid and stirred for 1 hour and 420 ml of pre-distilled n-Heptane is charged slowly to the solution. The solution I stirred for 1 hour at 20-30° C. and cooled at 0-10° C. The crystallized material is filtered. The wet cake is washed with the 2:1 mixture of 420 ml n-Heptane and Dichloromethane and suck dried for 2 hour. The solid material is dried for at 70-80° C. under vacuum for 16-18 hours to get Form-1 of Cabazitaxel.
Yield: 86%
Chromatographic Purity: 99.8%

Example-3

Charged Cabazitaxel (1.0 g) and DMSO (5 mL) and stirred to dissolve the solid. Charged the Cabazitaxel solution into water (50 mL) under stirring at 20-25° C. Reaction mixture was stirred for 1 h at 20-25° C. Filter the obtained solid and washed with water (20 mL). Material was dried for 1 h at room temperature and 50-55° C. for 6 h under 0-10 mbar to get Form-2 of Cabazitaxel.
DSC −68.50° C., 114.59° C., 174.12° C.
TGA −5.88 (up to 105° C.)
Moisture −2.70% w/w
Purity −92.42%

Example-4

Charged Cabazitaxel (1.0 g) and Acetonitrile (10 mL) and stirred to dissolve the solid. Charged the Cabazitaxel solution into water (20 mL) under stirring at 20-25° C. Reaction mixture was stirred for 1 h at 20-25° C. Filter the obtained solid and washed with water (20 mL). Material was dried for 1 h at room temperature and 50-55° C. for 6 h under 0-10 mbar to get Form-3 of Cabazitaxel.
DSC −71.59° C., 153.07° C.
TGA −1.438% (up to 105° C.)
Moisture −4.10% w/w
Purity −94.53%

Example-5

Charged Cabazitaxel (1.0 g) and DMSO (5 mL) and stirred to dissolve the solid. To this solution Charged Water (20 mL) under stirring at 20-25° C. and stirred for 1 h min at 20-25° C. Filter the obtained solid and washed with water (20 mL). Material was dried for 1 h at room temperature and 50-55° C. for 6 h under 0-10 mbar to get Form-4 of Cabazitaxel.
DSC −45.35° C. and 124.92° C.
TGA −4.816% (up to 105° C.)
Moisture −2.09% w/w
Purity −92.03%

Example-6

Charged Cabazitaxel (1.0 g) and Methanol (5 mL) and stirred to dissolve the solid. Charged the Cabazitaxel solution into water (20 mL) under stirring at 20-25° C. Reaction mixture was stirred for 1 h at 20-25° C. Filter the obtained solid and washed with water (20 mL). Material was dried for 1 h at room temperature and 45-50° C. for 6 h under 0-10 mbar to get Form-5 of Cabazitaxel.
DSC −56.29° C., 145.47° C.
TGA −0.970% (up to 105° C.)
Moisture −3.24% w/w
Purity −92.32%

Example-7

Charged Ethyl acetate (300 mL) and HCl (35% w/w, 1.93 g) and cooled the reaction mass 0-5° C. Charged 4α-acetoxy-2α-benzoyloxy-5β,20-epoxy-1β,13α-dihydroxy-7β,10β-dimethoxy-9-oxo-11-taxen-13α-yl-(2R,4S,5S)-3-tert-butoxycarbonyl-2-(4-methoxyphenyl)-4-phenyl-1,3-oxazolidine-5-carboxylate (10.0 g) to the reaction mixture under stirring at 0-5° C. and reaction mixture was stirred for 5-6 h at 0-5° C. Charged sodium bisulphite solution (25.0 g in 100 mL water) to the reaction mixture and stirred for 2 h at 0-5° C. Separated the organic layer followed by two time water washing (100 mL×2). Concentrate the organic layer on rotavapor at 45-50° C. under reduced pressure. Charged the toluene (50 mL) stirred at 20-25° C. for 1 hour and kept at 0-5° C. over night. Filter the solid and washed with two time toluene (50 mL×2 at 0-5° C.). Suck dried for 2 h and oven dried at 45-50° C. for 6 h under 0-10 mbar to obtain Form-6 of Cabazitaxel.
DSC −157.26° C.
TGA −4.00% (up to 105° C.)

Example-8

Charged Cabazitaxel (1.0 g) and Tetrahydrofuran (5 mL) and stirred to dissolve the solid. Charged the Cabazitaxel solution into n-Hexane (20 mL) under stirring at 20-25° C. Reaction mixture was stirred for 1 h at 20-25° C. Filter the obtained solid and washed with water (20 mL). Material was dried for 1 h at room temperature and at 45-50° C. for 6 h under 0-10 mbar to get Form-7 of Cabazitaxel.
DSC −162.00° C.
TGA −1.902% (up to 105° C.)

Example-9

Charged Cabazitaxel (1.0 g) and Ethyl acetate (50 mL) and stirred at 35-40° C. to dissolve the solid. Reaction mixture was distilled till about half of the volume (25 ml). To this Charged n-Hexane (75 mL) under stirring at 20-25° C. Reaction mixture was stirred for 2 h min at 20-25° C. Filter the obtained solid and washed with n-Hexane (25 mL). Material was dried for 1-2 hour at room temperature and 45-50° C. for 6 h under 0-10 mbar to get Form-8 of Cabazitaxel.
DSC −151.84° C., 159.08° C.
TGA −7.126 (up to 105° C.)
Purity −95.28%

Example-10

Charged Cabazitaxel (800 mg) and Ethyl acetate (40 mL) and stirred at 35-40° C. and further at 40-45° C. for 2 hours to get the complete dissolution. Obtained material was dried for 2 hours at 45-50° C. for 6 h under 0-10 mbar to get Form-9 of Cabazitaxel.
DSC −156.51° C.
TGA −3.314% (up to 105° C.)
Purity −87.45%

Example-11

Charged Cabazitaxel (0.9 g) and Tetrahydrofuran (2.7 mL) and stirred to dissolve the solid. Charged Cabazitaxel solution into Methyl tertiary-butyl ether (70 mL) under stirring at 20-25° C. Reaction mixture was stirred for overnight at 20-25° C. Filter the obtained solid and washed with Methyl tertiary-butyl ether (10 mL). Material was dried for 1 hour at room temperature and at 45-50° C. for 6 h under 0-10 mbar to get Form-10 of Cabazitaxel.

Example-12

Charged Cabazitaxel (0.9 g) and Dichloromethane (1.35 mL) and stirred to dissolve the solid. Charged Methyl tertiary-butyl ether (60 mL) and stirred at 20-25° C. for 1 hour. Filter the obtained solid and washed with Methyl tertiary-butyl ether (10 mL). Material was dried for 1 hour at room temperature and at 45-50° C. for 6 h under 0-10 mbar to get Form-11 of Cabazitaxel.
DSC −162.26° C.
TGA −1.912% (up to 105° C.)
Purity −95.59%

Example-13

Charged Cabazitaxel (1.0 g) and Dichloromethane (25 ml). Reaction mixture was left at RT for 2 day without stirring. The solvent got evaporated and material crystallized as solid. Solid material was dried for 6 h at 50-55° C. under 0-10 mbar pressure in a vacuum oven to get Form-12 of Cabazitaxel.
DSC −150.47° C.
TGA −4.03% (up to 105° C.)
Purity −91.82%

Example-14

Charged Cabazitaxel (5.0 g) and Acetonitrile (25 ml). Reaction mixture was heated at 55-60° C. to dissolve the solid and cooled up to RT and stirred for 2 hours. Reaction mixture was left at room temperature without stirring. Solid material was filtered and washed with acetonitrile (25 ml). Material was dried at room temperature for 30 min and dried for 6 h at 50-55° C. under 0-10 mbar pressure in a vacuum oven to get Form-13 of Cabazitaxel.
DSC −119.57° C.
TGA −3.058 (up to 105° C.)
Purity −97.53%

We claim:

1. A crystalline Form-1 of Cabazitaxel characterized by at least one of:
    a) an X-ray powder diffraction (XRD) pattern having peaks at 7.27, 8.098, 8.9288, 9.8386, 10.3719, 11.1279, 12.6872, 12.9551, 14.3024, 15.3175, and 15.7891±0.2 degrees two-theta, and
    b) an X-ray powder diffraction (XRD) pattern as depicted in FIG. 1.

2. A process for preparing crystalline Cabazitaxel Form-1 of claim 1, which comprises:
    a) dissolving crude Cabazitaxel in chlorinated hydrocarbon;
    b) adding aliphatic hydrocarbon solvent to the solution obtained in step (a); and
    c) isolating Cabazitaxel crystalline Form-1.

3. The process of claim 2, wherein chlorinated hydrocarbon is dichloromethane.

4. The process of claim 2, wherein aliphatic hydrocarbon is n-Hexane or heptane.

5. A crystalline Form-2 of Cabazitaxel characterized by at least one of:
    an X-ray powder diffraction (XRD) pattern having peaks at about 3.9477, 6.9328, 7.8516, 10.1685, 10.7552, 11.6174, 12.1755, 12.8255, 13.5716, 14.0264, 15.1085, 17.2533 and 18.1414±0.2 degrees two-theta;
    an X-ray powder diffraction (XRD) pattern as depicted in FIG. 3;
    melting endotherms of 68.5, 114.59 and 174° C. as measured by differential scanning calorimetry; and
    a weight loss of about 5.88 w/w, as measured by a Thermo gravimetric analysis (TGA).

6. A process for preparing crystalline Cabazitaxel Form-2 of claim 5, which comprises:
    a) dissolving crude Cabazitaxel in dimethyl sulfoxide;
    b) adding water to the solution obtained in step (a); and
    c) isolating Cabazitaxel crystalline Form-2.

7. A crystalline Form-3 of Cabazitaxel characterized by at least one of:
    an X-ray powder diffraction (XRD) pattern having peaks at 4.2517, 6.9143, 7.5307, 8.5018, 8.6671, 10.0963, 11.016, 11.7729, 12.2981, 12.655, 13.2716, 13.3755, 13.8385, 14.3319, 15.1075 and 15.5934 degrees two theta ±0.2 degrees two-theta;
    an X-ray powder diffraction (XRD) pattern as depicted in FIG. 5;
    a melting endotherm of 71.59° C. as measured by differential scanning calorimetry; and
    a weight loss of about 1.44 w/w, as measured by a Thermo gravimetric analysis (TGA).

8. A process for preparing crystalline Cabazitaxel Form-3 of claim 7, which comprises:
    a) dissolving crude Cabazitaxel in Acetonitrile;
    b) adding water to the solution obtained in step (a); and
    c) isolating Cabazitaxel crystalline Form-3.

9. A crystalline Form-4 of Cabazitaxel characterized by at least one of:
    an X-ray powder diffraction (XRD) pattern having peaks at 6.9147, 7.9157, 10.1788, 10.7274, 12.2545, 13.9828, 15.1051, 17.2041, 18.1419, 19.7907, 21.5114, 23.1898, 24.6259, 25.3476 and 35.589 degrees two theta ±0.2 degrees two-theta;
    an X-ray powder diffraction (XRD) pattern as depicted in FIG. 7;
    melting endotherms of 45.35 and 124.92° C. as measured by differential scanning calorimetry; and
    a weight loss of about 4.82 w/w, as measured by a Thermo gravimetric analysis (TGA).

10. A process for preparing crystalline Cabazitaxel Form-4 of claim 9, which comprises:
    a) dissolving crude Cabazitaxel in DMSO;
    b) adding the solution obtained in step (a) in to water; and
    c) isolating Cabazitaxel crystalline Form-4.

11. A crystalline Form-5 of Cabazitaxel characterized by at least one of:
    an X-ray powder diffraction (XRD) pattern having peaks at 7.4653, 7.9088, 8.632, 10.0056, 10.1441, 12.6034, 12.8787, 13.3288, 13.7267, 14.0979, 14.7919, 14.9815, 15.8132, 16.6686, 17.0039, 17.4065, 17.565, 17.9825, 18.8633, 19.4114, 20.0775, 20.3849, 20.8302, 21.5334, 21.9088, 22.3894, 22.8016, 23.8831, 24.4216, 25.3046, 26.0013, 26.5986, 27.1112, 27.6563, 28.1144, 28.4627, 29.3176, 29.9773, 30.3352, 30.7862, 31.6162, 32.0435, 32.7366, 34.0162, 34.4257, 35.2812, 35.6799, 36.3708, 37.2971, 37.9603 and 39.4846 degrees two theta ±0.2 degrees two-theta;
    an X-ray powder diffraction (XRD) pattern as depicted in FIG. 9;
    melting endotherms of 56.29 and 145.27° C. as measured by differential scanning calorimetry;
    and a weight loss of about 0.97 w/w, as measured by a Thermo gravimetric analysis (TGA).

12. A process for preparing crystalline Cabazitaxel Form-5 of claim 11, which comprises:
    a) dissolving crude Cabazitaxel in Methanol;
    b) adding water to the solution obtained in step (a); and
    c) isolating Cabazitaxel crystalline Form-5.

13. A crystalline Form-6 of Cabazitaxel characterized by at least one of:
    an X-ray powder diffraction (XRD) pattern having peaks at 7.5382, 7.8933, 8.5705, 9.0313, 9.9955, 12.53567, 12.7543, 13.1642, 13.8096, 14.1239, 14.9894, 15.1341, 15.5073, 15.8243, 15.9533, 16.6157, 16.8378, 17.3433, 17.8146, 18.7843, 19.6295, 20.0721, 20.272, 20.6837, 21.6467, 22.0733, 22.4547, 22.8002, 23.352, 23.8517, 24.4177, 25.2362, 25.9305, 26.3936, 26.9242, 27.4422, 27.8523, 28.2344, 28.8554, 30.1018, 30.9761, 31.3884, 32.409, 33.0368, 34.1981, 34.9906, 36.1324, 36.5453, 37.1655, 37.8404 and 38.3193 degrees two theta ±0.2 degrees two-theta;

an X-ray powder diffraction (XRD) pattern as depicted in FIG. 11; a melting endotherm of 157.26° C. as measured by differential scanning calorimetry; and a weight loss of about 4.0 w/w, as measured by a Thermo gravimetric analysis (TGA).

14. A process for preparing crystalline Cabazitaxel Form-6 of claim 13, which comprises:
    a) dissolving crude Cabazitaxel in toluene;
    b) cooling the solution obtained in step (a) in refrigerator at 0-5° C.; and
    c) isolating Cabazitaxel crystalline Form-6.

15. A crystalline Form-7 of Cabazitaxel characterized by at least one of:
    an X-ray powder diffraction (XRD) pattern having peaks at about 5.1654, 6.0558, 7.5462, 7.7852, 8.8713, 9.5395, 10.1166, 10.3287, 10.7561, 11.3142, 11.6744, 11.7668, 12.0871, 12.5438, 12.7839, 13.0253, 13.3688, 14.147, 14.4314, 15.2768, 15.4254, 15.7276, 16.0658, 16.7552, 17.1127, 17.633, 18.0978, 18.5174, 18.9323, 19.6057, 20.309, 21.0129, 21.3404, 21.8444, 22.3403, 22.7858, 23.4707, 24.0622, 24.479, 25.1489, 25.6754, 26.632, 27.1126, 27.884, 28.8493, 30.3359, 30.7151, 31.6619, 32.6055, 33.4331, 35.9047, 36.7957, 37.5168 and 38.4523 degrees two theta ±0.2 degrees two-theta; an X-ray powder diffraction (XRD) pattern as depicted in FIG. 13;
    a melting endotherm of 162° C. as measured by differential scanning calorimetry;
    and a weight loss of about 1.902 w/w, as measured by a Thermo gravimetric analysis (TGA).

16. A process for preparing crystalline Cabazitaxel Form-7 of claim 15, which comprises:
    a) dissolving crude Cabazitaxel in tetrahydrofuran;
    b) adding aliphatic hydrocarbon solvent to the solution obtained in step (a); and
    c) isolating Cabazitaxel crystalline Form-5.

17. The process of claim 16, wherein in step (b) the aliphatic hydrocarbon is n-hexane.

18. A crystalline Form-8 of Cabazitaxel characterized by at least one of: an X-ray powder diffraction (XRD) pattern having peaks at 7.4653, 7.9088, 8.632, 10.0056, 10.1441, 12.6034, 12.8787, 13.3288, 13.7267, 14.0979, 14.7919, 14.9815, 15.8132, 16.6686, 17.0039, 17.4065, 17.565, 17.9825, 18.8633, 19.4114, 20.0775, 20.3849, 20.8302, 21.5334, 21.9088, 22.3894, 22.8016, 23.8831, 24.4216, 25.3046, 26.0013, 26.5986, 27.1112, 27.6563, 28.1144, 28.4627, 29.3176, 29.9773, 30.3352, 30.7862, 31.6162, 32.0435, 32.7366, 34.0162, 34.4257, 35.2812, 35.6799, 36.3708, 37.2971, 37.9603 and 39.4846 degrees two theta ±0.2 degrees two-theta;
    an X-ray powder diffraction (XRD) pattern as depicted in FIG. 15; by a melting endotherms of 151.84 and 159.08° C. as measured by differential scanning calorimetry; and by a weight loss of about 7.126 w/w, as measured by a Thermo gravimetric analysis (TGA).

19. A process for preparing crystalline Cabazitaxel Form-8 of claim 18, which comprises:
    a) dissolving crude Cabazitaxel in ethyl acetate;
    b) adding aliphatic hydrocarbon solvent to the solution obtained in step (a); and
    c) isolating Cabazitaxel crystalline Form-8.

20. The process of claim 19, wherein in step (b) the aliphatic hydrocarbon is n-hexane.

21. A crystalline Form-9 of Cabazitaxel characterized by:
    an X-ray powder diffraction (XRD) pattern having peaks at about 7.4888, 7.8964, 14.9996, 15.8372, 18.1238, 19.4223, 20.0681, 22.578, 23.88, 27.0807 and 34.2049 degrees two theta ±0.2 degrees two-theta;
    an X-ray powder diffraction (XRD) pattern as depicted in FIG. 17;
    by a melting endotherm 156.51° C. as measured by differential scanning calorimetry; and
    by a weight loss of about 3.31 w/w, as measured by a Thermo gravimetric analysis (TGA).

22. A process for preparing crystalline Cabazitaxel Form-9 of claim 21, which comprises:
    a) dissolving crude Cabazitaxel in ethyl acetate;
    b) distillation of the solution of step (a) at a suitable temperature; and
    c) isolating Cabazitaxel crystalline Form-9.

23. A crystalline Form-10 of Cabazitaxel characterized by at least one of:
    an X-ray powder diffraction (XRD) pattern having peaks at 7.3698, 7.667, 8.8401, 10.0932, 10.1915, 12.1842, 12.5108, 12.6905, 13.2027, 13.4312, 14.3957, 14.7872, 15.2618, 15.6302, 16.206, 16.8942, 17.6122, 17.9955, 18.4562, 18.6846, 19.3745, 19.7227, 20.2884, 20.9802, 21.1714, 21.6056, 21.779, 22.268, 22.595, 23.1582, 23.3974, 23.7276, 24.5077, 25.003, 25.3184, 25.7709, 26.1442, 26.286, 26.7247, 26.9795, 27.7495, 28.3621, 28.6729, 28.8427, 30.0072, 30.2711, 30.6479, 30.9287, 31.3812, 33.572, 34.6909, 35.3171, 35.8341, 36.2362, 36.6585, 37.3182, 39.0095 degrees two theta ±0.2 degrees two-theta;
    an X-ray powder diffraction (XRD) pattern as depicted in FIG. 19; a melting endotherm of 163.24° C. as measured by differential scanning calorimetry; and
    a weight loss of about 1.39 w/w, as measured by a Thermo gravimetric analysis (TGA).

24. A process for preparing crystalline Cabazitaxel Form-10 of claim 23, which comprises:
    a) dissolving crude Cabazitaxel in tetrahydrofuran;
    b) adding methyl tert-butyl ether to the solution obtained in step (a); and
    c) isolating Cabazitaxel crystalline Form-10.

25. A crystalline Form-11 of Cabazitaxel characterized by at least one of:
    an X-ray powder diffraction (XRD) pattern having peaks at 7.3745, 7.6642, 8.8442, 10.0941, 12.1815, 12.5115, 12.6887, 13.1938, 13.4343, 14.4048, 14.7832, 15.2664, 15.6318, 16.1844, 16.8979, 17.6182, 17.9285, 17.9944, 18.4383, 18.6827, 19.3607, 19.69, 20.2846, 20.9841, 21.1786, 21.2743, 21.5948, 21.7825, 22.0077, 22.2638, 22.5902, 23.1399, 23.4095, 23.6935, 24.511, 25.0016, 25.2019, 25.779, 26.2666, 26.9532, 27.728, 28.2877, 28.6692, 30.0142, 30.6341, 30.9294, 31.3636, 33.5386, 34.0535, 34.6503, 35.7594, 36.2287, 36.6173, 37.5314 and 39.0013 degrees two theta ±0.2 degrees two-theta;

an X-ray powder diffraction (XRD) pattern as depicted in FIG. 21; a melting endotherm of 162.26° C. as measured by differential scanning calorimetry; and a weight loss of about 1.91 w/w, as measured by a Thermo gravimetric analysis (TGA).

26. A process for preparing crystalline Cabazitaxel Form-11 of claim 25, which comprises:
    a) dissolving crude Cabazitaxel in Dichloromethane;
    b) adding methyl tert-butyl ether to the solution obtained in step (a); and
    c) isolating Cabazitaxel crystalline Form-11.

27. A crystalline Form-12 of Cabazitaxel characterized by at least one of:
    an X-ray powder diffraction (XRD) pattern having peaks at 7.2416, 7.3725, 7.7374, 8.0736, 8.9401, 9.8027, 10.3081, 11.0522, 12.5684, 12.9213, 13.2282, 13.5547, 14.2406, 14.4855, 14.8101, 15.105, 15.2813, 15.6609, 16.3001, 17.1182, 17.5246, 17.7526, 18.4631, 18.7094, 19.4528, 19.7879, 20.4143, 21.2813, 21.9409, 22.362, 22.5558, 22.9703, 23.7148, 24.2623, 25.328, 25.7613, 26.126, 27.2233, 27.8554, 29.3835, 30.3838, 30.884, 31.483, 32.2384, 33.7493, 36.45, 37.8297 and 39.072 degrees two theta ±0.2 degrees two-theta; an X-ray powder diffraction (XRD) pattern as depicted in FIG. 23;
    a melting endotherm of 150.47° C. as measured by differential scanning calorimetry; and
    a weight loss of about 4.03 w/w, as measured by a Thermo gravimetric analysis (TGA).

28. A process for preparing crystalline Cabazitaxel Form-12 of claim 27, which comprises:
    a) dissolving crude Cabazitaxel in dichloromethane;
    b) keeping the solution obtained in step (a) at ambient temperature for 2 days; and
    c) isolating Cabazitaxel crystalline Form-12.

29. A crystalline Form-13 of Cabazitaxel characterized by at least one of: an X-ray powder diffraction (XRD) pattern having peaks at 7.6407, 8.2470, 8.9083, 9.6908, 10.2052, 10.8975, 11.7467, 12.5726, 13.1374, 13.6142, 14.5568, 14.7306, 15.1414, 15.3346, 15.8172, 15.9783, 16.1685, 16.5428, 17.0081, 17.4437, 17.7617, 18.3039, 18.6969, 19.2043, 19.3552, 19.8813, 20.5800, 21.1902, 21.6304, 21.8210, 22.6461, 23.0075, 23.3798, 23.6649, 24.227, 24.6723, 24.8109, 25.2951, 25.7631, 26.3656, 26.7471, 27.009, 27.2631, 27.4812, 28.0822, 28.9015, 29.2351, 29.4124, 29.9002 and 30.3023 degrees two theta ±0.2 degrees two-theta;
    an X-ray powder diffraction (XRD) pattern as depicted in FIG. 25; a melting endotherm of 119.57° C. as measured by differential scanning calorimetry; and
    a weight loss of about 3.058 w/w, as measured by a Thermo gravimetric analysis (TGA).

30. A process for preparing crystalline Cabazitaxel Form-13 of claim 29, which comprises:
    a) dissolving crude Cabazitaxel in acetonitrile;
    b) keeping the solution obtained in step (a) at ambient temperature for 2 days; and
    c) isolating Cabazitaxel crystalline Form-13.

* * * * *